(12) United States Patent
Reed et al.

(10) Patent No.: US 11,253,193 B2
(45) Date of Patent: Feb. 22, 2022

(54) UTILIZATION OF VOCAL ACOUSTIC BIOMARKERS FOR ASSISTIVE LISTENING DEVICE UTILIZATION

(71) Applicants: Kieran Reed, Macquarie University (AU); John Michael Heasman, East Melbourne (AU); Kerrie Plant, Macquarie University (AU); Alex Von Brasch, Macquarie University (AU); Stephen Fung, Macquarie University (AU)

(72) Inventors: Kieran Reed, Macquarie University (AU); John Michael Heasman, East Melbourne (AU); Kerrie Plant, Macquarie University (AU); Alex Von Brasch, Macquarie University (AU); Stephen Fung, Macquarie University (AU)

(73) Assignee: Cochlear Limited, Macquarie University (AU)

(*) Notice: Subject to any disclaimer, the term of this patent is extended or adjusted under 35 U.S.C. 154(b) by 1087 days.

(21) Appl. No.: 15/346,039

(22) Filed: Nov. 8, 2016

(65) Prior Publication Data
US 2018/0125415 A1 May 10, 2018

(51) Int. Cl.
*A61B 5/00* (2006.01)
*H04R 25/00* (2006.01)
(Continued)

(52) U.S. Cl.
CPC ............ *A61B 5/4803* (2013.01); *A61B 5/125* (2013.01); *A61B 7/04* (2013.01); *H04R 25/30* (2013.01);
(Continued)

(58) Field of Classification Search
CPC ..... A61B 5/4803; A61B 5/125; A61B 5/4836; A61B 5/7282; H04R 25/505; H04R 25/30;
(Continued)

(56) References Cited

U.S. PATENT DOCUMENTS 3,676,595 A * 7/1972 Dolansky ............... G09B 19/04
704/276
4,731,850 A * 3/1988 Levitt ....................... H03G 5/16
381/317

(Continued)

FOREIGN PATENT DOCUMENTS

JP 2005531175 A 10/2005
KR 10-2000-0064472 A 11/2000
(Continued)

OTHER PUBLICATIONS

Communication Tips for the Heard of Hearing and their Family and Friends, the Cork Deaf Association, https://www.corkdeaf.ie/wp-content/uploads/2014/03/Communication-Tips-for-Hard-of-Hearing-and-Family-and-Friends-publicationpdf.pdf, 2013 (Year: 2013).*

(Continued)

*Primary Examiner* — Sean P Dougherty
(74) *Attorney, Agent, or Firm* — Pilloff Passino & Cosenza LLP; Martin J. Cosenza

(57) ABSTRACT

A body worn or implantable hearing prosthesis, including a device configured to capture an audio environment of a recipient and evoke a hearing percept based at least in part on the captured audio environment, wherein the hearing prosthesis is configured to identify, based on the captured audio environment, one or more biomarkers present in the audio environment indicative of the recipient's ability to hear.

25 Claims, 21 Drawing Sheets

(51) Int. Cl.
  *A61B 5/12* (2006.01)
  *A61B 7/04* (2006.01)
(52) U.S. Cl.
  CPC .......... H04R 25/505 (2013.01); H04R 25/507 (2013.01); *A61B 5/4836* (2013.01); *A61B 5/4842* (2013.01); *A61B 5/7282* (2013.01); *A61B 5/742* (2013.01); *A61B 5/7475* (2013.01); *H04R 25/606* (2013.01); *H04R 2225/41* (2013.01); *H04R 2225/43* (2013.01)
(58) Field of Classification Search
  CPC .............. H04R 25/606; H04R 2225/43; H04R 2225/41
  See application file for complete search history.

(56) References Cited

U.S. PATENT DOCUMENTS

| | | | |
|---|---|---|---|
| 5,729,658 | A | 3/1998 | Hou et al. |
| 5,824,022 | A | 10/1998 | Zilberman et al. |
| 5,825,894 | A | 10/1998 | Shennib |
| 5,923,764 | A | 7/1999 | Shennib |
| 5,999,856 | A * | 12/1999 | Kennedy ............ A61N 1/36036 381/60 |
| 6,563,931 | B1 * | 5/2003 | Soli ...................... H04R 25/505 381/318 |
| 6,628,795 | B1 * | 9/2003 | Ludvigsen ........... H04R 25/356 381/107 |
| 7,027,606 | B2 | 4/2006 | DAgri |
| 7,043,303 | B1 | 5/2006 | Overstreet |
| 7,171,272 | B2 * | 1/2007 | Blarney ............. A61N 1/36038 607/57 |
| 7,206,416 | B2 | 4/2007 | Krause et al. |
| 8,010,366 | B1 | 8/2011 | Kearby et al. |
| 8,036,898 | B2 | 10/2011 | Sato et al. |
| 8,533,001 | B2 | 9/2013 | Skiba |
| 8,568,145 | B2 | 10/2013 | Jastrzembski et al. |
| 8,708,702 | B2 | 4/2014 | Paul |
| 8,737,571 | B1 | 5/2014 | Seeley et al. |
| 8,963,987 | B2 | 2/2015 | Byun et al. |
| 9,173,043 | B2 | 10/2015 | Bulow et al. |
| 9,363,614 | B2 | 6/2016 | Jepsen et al. |
| 9,560,991 | B2 | 2/2017 | de Vries et al. |
| 9,592,382 | B2 | 3/2017 | Kulkarni |
| 9,814,879 | B2 | 11/2017 | Banna et al. |
| 2002/0012438 | A1 * | 1/2002 | Leysieffer ........... H04R 25/507 381/312 |
| 2002/0035309 | A1 * | 3/2002 | Leysieffer ........... H04R 25/606 600/25 |
| 2002/0062059 | A1 * | 5/2002 | Waldmann ............ H04R 25/70 600/25 |
| 2002/0191799 | A1 * | 12/2002 | Nordqvist ............ H04R 25/505 381/60 |
| 2005/0027537 | A1 | 2/2005 | Krause et al. |
| 2005/0107844 | A1 * | 5/2005 | Van Den Honert ........................ A61N 1/36038 607/57 |
| 2005/0129262 | A1 | 6/2005 | Dillon et al. |
| 2006/0029912 | A1 | 2/2006 | Kearby et al. |
| 2006/0093997 | A1 | 5/2006 | Kearby et al. |
| 2006/0287690 | A1 * | 12/2006 | Bouchataoui ...... A61N 1/36039 607/57 |
| 2007/0027676 | A1 | 2/2007 | Chambers et al. |
| 2007/0093878 | A1 | 4/2007 | Edge et al. |
| 2008/0124685 | A1 | 5/2008 | Chalupper |
| 2008/0194984 | A1 * | 8/2008 | Keefe .................... A61B 5/121 600/559 |
| 2008/0212789 | A1 | 9/2008 | Cronin et al. |
| 2008/0261776 | A1 | 10/2008 | Skiba |
| 2009/0154741 | A1 | 6/2009 | Woods et al. |
| 2009/0154743 | A1 | 6/2009 | Lundh et al. |
| 2009/0191521 | A1 * | 7/2009 | Paul ..................... G10L 17/16 434/169 |
| 2009/0245556 | A1 * | 10/2009 | Parker ................... H04R 25/70 381/326 |
| 2009/0306225 | A1 * | 12/2009 | Lighter ................ A61K 9/0046 514/772.1 |
| 2009/0306457 | A1 * | 12/2009 | Parker .................. H04R 25/606 600/25 |
| 2010/0020993 | A1 * | 1/2010 | Poh ...................... H04R 25/505 381/314 |
| 2010/0069998 | A1 | 3/2010 | Saoji et al. |
| 2010/0145411 | A1 | 6/2010 | Spitzer |
| 2010/0152813 | A1 | 6/2010 | Lineaweaver et al. |
| 2010/0196861 | A1 * | 8/2010 | Lunner ................ H04R 25/505 434/112 |
| 2010/0280307 | A1 * | 11/2010 | Lineaweaver ..... A61N 1/36036 600/25 |
| 2010/0296661 | A1 | 11/2010 | Goorevich et al. |
| 2011/0019849 | A1 * | 1/2011 | Nielsen ................ H04R 25/558 381/322 |
| 2011/0082519 | A1 | 4/2011 | Strahl et al. |
| 2011/0150253 | A1 | 6/2011 | Corona-Strauss et al. |
| 2011/0200217 | A1 | 8/2011 | Gurin |
| 2011/0256513 | A1 * | 10/2011 | Levitt .................... G06Q 10/00 434/185 |
| 2011/0257994 | A1 | 10/2011 | Givens et al. |
| 2011/0313315 | A1 | 12/2011 | Attias et al. |
| 2012/0029593 | A1 | 2/2012 | Calle et al. |
| 2012/0064477 | A1 * | 3/2012 | Schmitt ................ A61B 6/145 433/29 |
| 2012/0077158 | A1 | 3/2012 | Jastrzembski et al. |
| 2012/0155664 | A1 | 6/2012 | Zhang et al. |
| 2012/0183163 | A1 * | 7/2012 | Apfel ..................... H04R 25/70 381/314 |
| 2012/0183165 | A1 * | 7/2012 | Foo ........................ H04R 25/50 381/314 |
| 2012/0215532 | A1 | 8/2012 | Foo et al. |
| 2012/0230502 | A1 * | 9/2012 | Nishizaki ............... H04R 25/70 381/60 |
| 2012/0300964 | A1 * | 11/2012 | Ku ..................... A61B 5/04845 381/321 |
| 2013/0064404 | A1 * | 3/2013 | Ridler .................. H04R 25/405 381/313 |
| 2013/0103113 | A1 | 4/2013 | Lineaweaver et al. |
| 2013/0109909 | A1 * | 5/2013 | van Gerwen .......... H04R 25/43 600/25 |
| 2013/0129125 | A1 * | 5/2013 | Meskens .............. H04R 25/606 381/314 |
| 2013/0137550 | A1 | 5/2013 | Skinner et al. |
| 2013/0202123 | A1 * | 8/2013 | Nishizaki ............... H04R 25/70 381/60 |
| 2013/0266165 | A1 * | 10/2013 | Neumeyer ............. H04R 25/30 381/314 |
| 2013/0274628 | A1 * | 10/2013 | Fausti ................... A61B 5/123 600/559 |
| 2014/0039576 | A1 | 2/2014 | Hillbralt |
| 2014/0050341 | A1 | 2/2014 | Flynn et al. |
| 2014/0107526 | A1 * | 4/2014 | Thibaut ................. A61B 7/005 600/559 |
| 2014/0153729 | A1 * | 6/2014 | Adachi ................. H04R 25/70 381/60 |
| 2014/0270210 | A1 | 9/2014 | van Dijk |
| 2014/0294188 | A1 * | 10/2014 | Rini ....................... A61B 5/048 381/60 |
| 2014/0309549 | A1 | 10/2014 | Selig et al. |
| 2014/0336448 | A1 | 11/2014 | Banna et al. |
| 2015/0023535 | A1 * | 1/2015 | Shennib ................. H04R 25/70 381/314 |
| 2015/0080980 | A1 * | 3/2015 | Meister .............. A61N 1/36038 607/57 |
| 2015/0157226 | A1 * | 6/2015 | Strahl ................. A61B 5/04845 600/554 |
| 2015/0172838 | A1 * | 6/2015 | Kuk ........................ A61B 5/00 381/314 |
| 2015/0173637 | A1 * | 6/2015 | Strahl ................... A61B 5/0031 600/554 |
| 2015/0215710 | A1 * | 7/2015 | Francart ................ H04R 25/552 381/326 |

(56) References Cited

U.S. PATENT DOCUMENTS

| | | | |
|---|---|---|---|
| 2015/0223734 A1* | 8/2015 | Schwarz | A61N 1/36039 600/554 |
| 2015/0281856 A1 | 10/2015 | Park et al. | |
| 2015/0304766 A1* | 10/2015 | Delikaris-Manias | G10L 21/0216 381/92 |
| 2015/0359468 A1* | 12/2015 | Bochner | A61B 5/123 600/559 |
| 2016/0001077 A1 | 1/2016 | Pontoppidan et al. | |
| 2016/0014531 A1* | 1/2016 | Hillbratt | H04R 25/505 381/318 |
| 2016/0080878 A1 | 3/2016 | Hillbratt et al. | |
| 2016/0140873 A1 | 5/2016 | Lineaweaver | |
| 2016/0144178 A1* | 5/2016 | Hillbratt | A61N 1/36038 607/57 |
| 2016/0166181 A1* | 6/2016 | Shennib | A61B 5/123 600/559 |
| 2016/0234609 A1* | 8/2016 | Bendsen | H04R 25/552 |
| 2016/0261959 A1* | 9/2016 | Harczos | H04R 25/353 |
| 2016/0262651 A1* | 9/2016 | Thai-Van | A61B 5/04012 |
| 2016/0345107 A1* | 11/2016 | Van Dijk | H04R 25/305 |
| 2016/0373869 A1* | 12/2016 | Gran | H04R 25/407 |
| 2016/0375244 A1* | 12/2016 | Schleich | A61N 1/36038 607/57 |
| 2017/0056655 A1* | 3/2017 | Lineaweaver | A61N 1/36039 |
| 2017/0064470 A1* | 3/2017 | Popovac | H04M 1/7253 |
| 2017/0072195 A1* | 3/2017 | Calle | A61N 1/37264 |
| 2017/0127201 A1 | 5/2017 | Roeck et al. | |
| 2017/0150909 A1* | 6/2017 | Dalhoff | A61B 5/125 |
| 2017/0201839 A1* | 7/2017 | Manchester | H04R 25/554 |
| 2017/0280254 A1* | 9/2017 | Chen | H04R 25/353 |
| 2017/0280257 A1* | 9/2017 | Gordon | H04R 25/558 |
| 2017/0304620 A1* | 10/2017 | Lineaweaver | A61N 1/36046 |
| 2017/0359659 A1 | 12/2017 | Von Brasch et al. | |
| 2017/0359661 A1* | 12/2017 | Goorevich | H04R 25/356 |
| 2017/0360364 A1 | 12/2017 | Heasman et al. | |
| 2017/0360365 A1* | 12/2017 | Heasman | A61B 5/04001 |
| 2018/0012511 A1* | 1/2018 | Reed | G09B 21/009 |
| 2018/0085581 A1* | 3/2018 | Fung | A61B 5/04001 |
| 2018/0091907 A1* | 3/2018 | Long | H04R 25/505 |
| 2018/0148456 A1* | 5/2018 | Clay | C07D 487/14 |
| 2018/0160984 A1* | 6/2018 | Mauger | A61B 5/7275 |
| 2018/0184215 A1* | 6/2018 | Oplinger | H04R 25/305 |
| 2018/0227676 A1* | 8/2018 | Glavin | H04R 25/505 |
| 2018/0352351 A1* | 12/2018 | Yoo | A61B 5/002 |
| 2019/0082275 A1* | 3/2019 | Andersen | H04R 25/505 |

FOREIGN PATENT DOCUMENTS

| | | |
|---|---|---|
| KR | 1020140081430 A | 7/2014 |
| KR | 1020140084744 A | 7/2014 |
| KR | 20150111157 A | 10/2015 |
| WO | 2005002431 A1 | 1/2005 |
| WO | 2009103823 A2 | 8/2009 |
| WO | 2015132692 A1 | 9/2015 |
| WO | 2016207860 A1 | 12/2016 |

OTHER PUBLICATIONS

Moberly, et al. "The Engima of Poor Performance by Adults With Cochlear Implants", Otology & Neurotology, 2016, vol. 37, pp. 1522-1528.

Sarampalis, et al. "Objective Measures of Listening Effort: Effects of Background Noise and Noise Reduction", Journal of Speech, Language, and Hearing Research, Oct. 2009, vol. 52, pp. 1230-1240.

Gosselin, et al. "Older adults expend more listening effort than young adults recognizing audiovisual speech in noise". Journal of Speech, Language, and Hearing Research, 2011, vol. 54, Issue 3, pp. 944-958, Montreal, Quebec, Canada.

Kelly Miles et al., "Acoustic Analysis of the Speech of an Australian English-speaking Child with Hearing Aids," Proceedings of the 14th Australasian International Conference on Speech Science and Technology, Dec. 2012.

Mary Joe Osberger et al., "Speech Production Characteristics of the Hearing Impaired," Speech and Language, Dec. 1982, pp. 227-288.

Tim Binsted, "ResApp on the road to diagnosis by smartphone," Sep. 30, 2015, http://www.theage.com.au/business/resapp-on-the-road-to-diagnosis-by-smartphone-20150929-gjxd8j, accessed Sep. 28, 2017.

https://web.archive.org/web/20161029124636/http://www.asha.org/PRPSpecificTopic.aspx?folderid=8589935321&section=Treatment, "Speech Sound Disorders-Articulation and Phonology," Oct. 29, 2016, American Speech-Language-Hearing Association.

https://minerva-access.unimelb.edu.au/handle/11343/39689, Oct. 2012, University of Melbourne, accessed Sep. 28, 2017.

James C. Mundt et al., "Vocal Acoustic Biomarkers of Depression Severity and Treatment Response," Biol Psychiatry, Oct. 1, 2012, vol. 72, No. 7.

International Search Report and Written Opinion for PCT/IB2017/056987, dated Apr. 23, 2018.

International Search Report and Written Opinion for PCT/IB2017/056987, dated Jun. 4, 2018.

* cited by examiner

UTILIZATION OF VOCAL ACOUSTIC BIOMARKERS FOR ASSISTIVE LISTENING DEVICE UTILIZATION

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In accordance with an exemplary embodiment, there is a body worn or implantable hearing prosthesis, comprising: a device configured to capture an audio environment of a recipient and evoke a hearing percept based at least in part on the captured audio environment, wherein the hearing prosthesis is configured to identify, based on the captured audio environment, one or more biomarkers present in the audio environment indicative of the recipient's ability.

In accordance with another exemplary embodiment, there is a method, comprising capturing sound with a hearing prosthesis, and evaluating the captured sound to determine the ability of the recipient of the hearing prosthesis to hear.

In accordance with another exemplary embodiment, there is a method, comprising capturing first sounds corresponding to speech of a recipient of a hearing prosthesis, comparing the captured first sounds to data based on speech of others, and diagnosing a hearing-related issue based on the comparison.

In accordance with another exemplary embodiment, there is a method, comprising, evaluating speech of a recipient of a hearing prosthesis, the speech of the recipient corresponding to speech produced by the recipient during a first temporal period, and adjusting a hearing habilitation and/or rehabilitation regime of the recipient based on the evaluation.

BRIEF DESCRIPTION OF THE DRAWINGS

Embodiments are described below with reference to the attached drawings, in which.

DETAILED DESCRIPTION

Figure 1A:
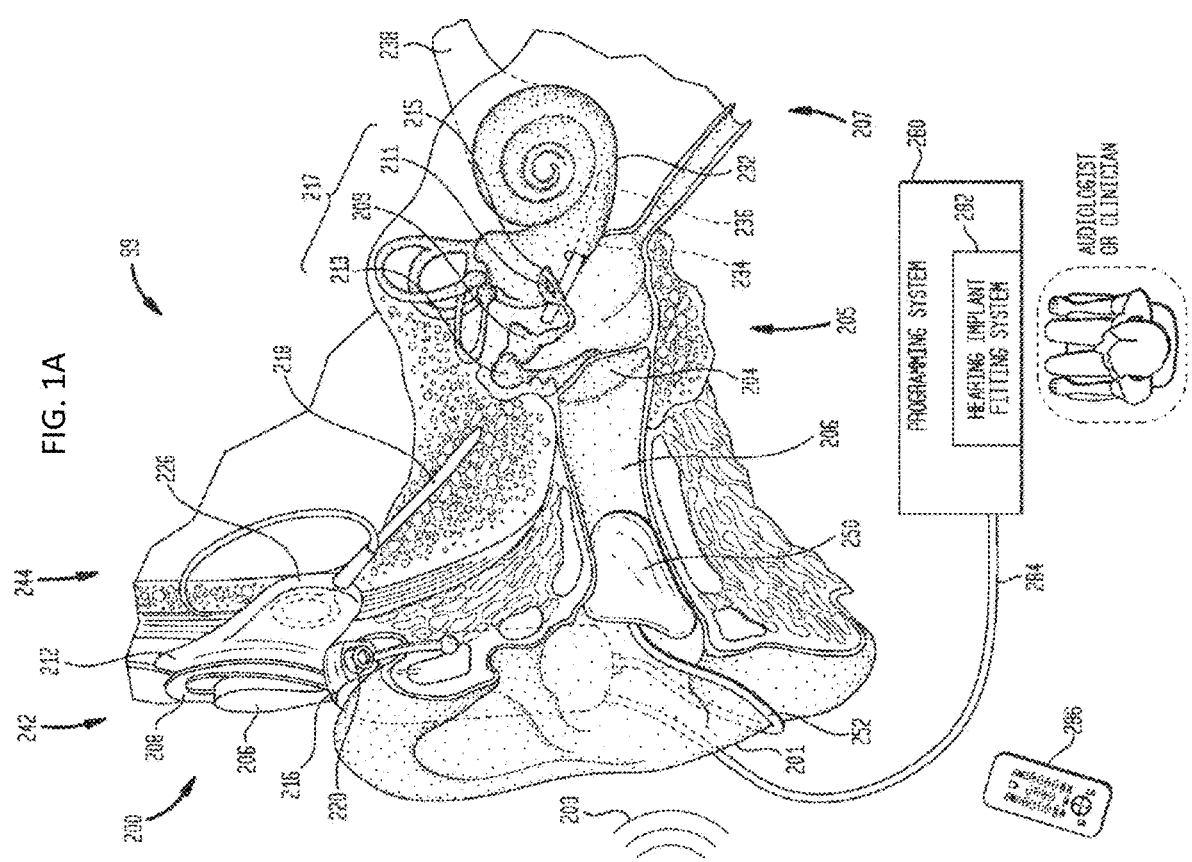
FIG. 1A is a perspective view of an exemplary multimodal hearing prosthesis according to an exemplary embodiment.

FIG. 1A is a perspective view of an exemplary multimodal prosthesis in which the present invention may be implemented. The ear 99 includes outer ear 201, middle ear 205, and inner ear 207 are described next below, followed by a description of an implanted multimodal system 200. Multimodal system 200 provides multiple types of stimulation, i.e., acoustic, electrical, and/or mechanical. These different stimulation modes may be applied ipsilaterally or contralaterally. In the embodiment shown in FIG. 1A, multimodal implant 200 provides acoustic and electrical stimulation, although other combinations of modes can be implemented in some embodiments. By way of example and not by way of limitation, a middle-ear implant can be utilized in combination with the cochlear implant, a bone conduction device can be utilized in combination with the cochlear implant, etc.

In a person with normal hearing or a recipient with residual hearing, an acoustic pressure or sound wave 203 is collected by outer ear 201 (that is, the auricle) and channeled into and through ear canal 206. Disposed across the distal end of ear canal 206 is a tympanic membrane 204 which vibrates in response to acoustic wave 203. This vibration is coupled to oval window, fenestra ovalis 215 through three bones of middle ear 205, collectively referred to as the ossicles 217 and comprising the malleus 213, the incus 209, and the stapes 211. Bones 213, 209, and 211 of middle ear 205 serve to filter and transfer acoustic wave 203, causing oval window 215 to articulate, or vibrate. Such vibration sets up waves of fluid motion within cochlea 232. Such fluid motion, in turn, activates tiny hair cells (not shown) that line the inside of cochlea 232. Activation of the hair cells causes appropriate nerve impulses to be transferred through the spiral ganglion cells (not shown) and auditory nerve 238 to the brain (not shown), where such pulses are perceived as sound.

Figure 1B:
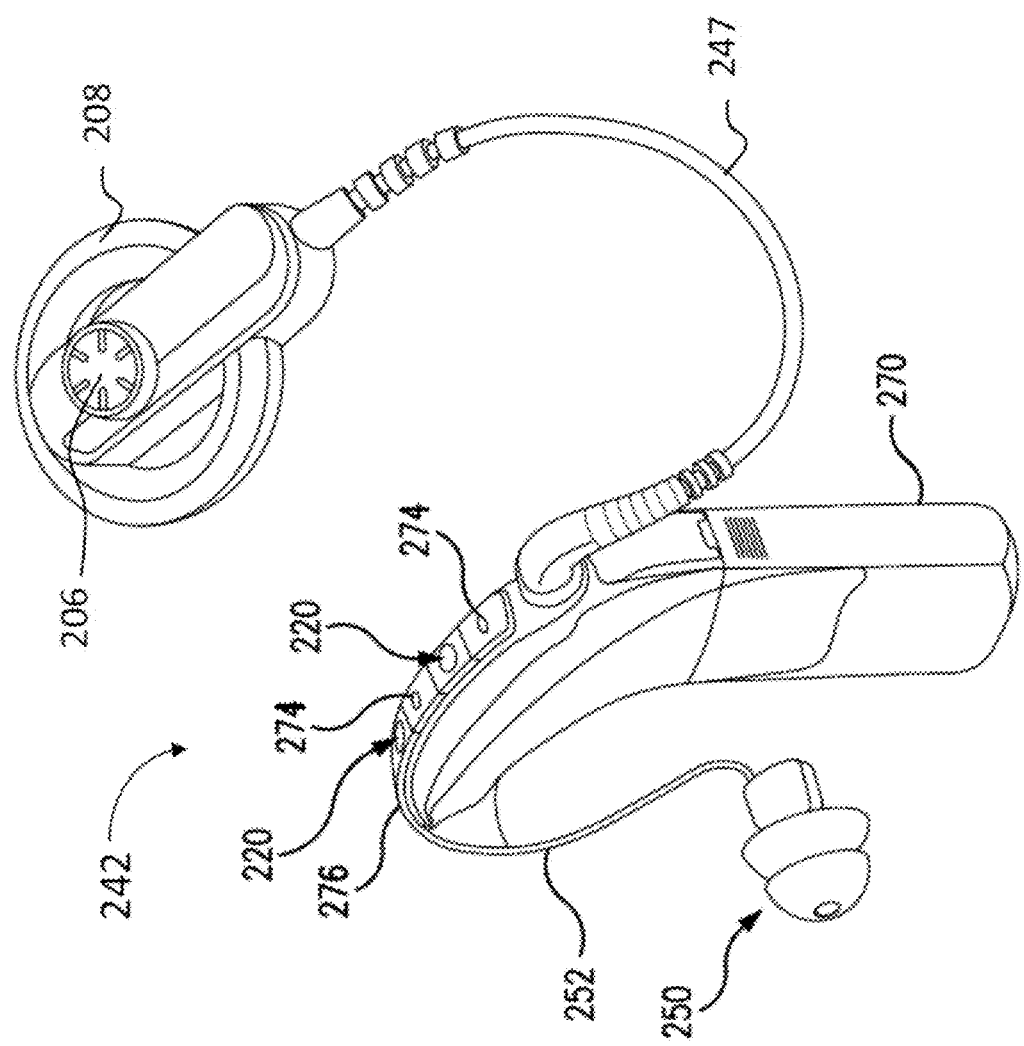
FIG. 1B is another view of the exemplary multimodal hearing prosthesis presented in FIG. 1A.

In individuals with a hearing deficiency who may have some residual hearing, an implant or hearing instrument may improve that individual's ability to perceive sound. Multimodal prosthesis 200 may comprises external component assembly 242 which is directly or indirectly attached to the body of the recipient, and an internal component assembly 244 which is temporarily or permanently implanted in the recipient. External component assembly is also shown in FIG. 1B. In embodiments of the present invention, components in the external assembly 242 may be included as part of the implanted assembly 244, and vice versa. Also, embodiments of the present invention may be used with implanted multimodal system 200 which are fully implanted.

External assembly 242 typically comprises a sound transducer 220 for detecting sound, and for generating an electrical audio signal, typically an analog audio signal. In this illustrative embodiment, sound transducer 220 is a microphone. In alternative embodiments, sound transducer 220 can be any device now or later developed that can detect sound and generate electrical signals representative of such sound.

Figure 1C:
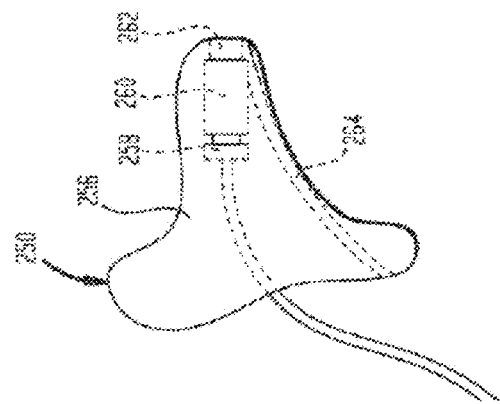
FIG. 1C provides additional details of the exemplary multimodal hearing prosthesis of FIG. 1B.

External assembly 242 also comprises a signal processing unit, a power source (not shown), and an external transmitter unit. External transmitter unit 206 comprises an external coil 208 and, preferably, a magnet (not shown) secured directly or indirectly to the external coil 208. Signal processing unit processes the output of microphone 220 that is positioned, in the depicted embodiment, by outer ear 201 of the recipient. Signal processing unit generates coded signals, referred to herein as a stimulation data signals, which are provided to external transmitter unit 206 via a cable 247 and to the receiver in the ear 250 via cable 252. FIG. 1C provides additional details of an exemplary receiver 250. The overall component containing the signal processing unit is, in this illustration, constructed and arranged so that it can fit behind outer ear 201 in a BTE (behind-the-ear) configuration, but may also be worn on different parts of the recipient's body or clothing.

In some embodiments, the signal processor may produce electrical stimulations alone, without generation of any acoustic stimulation beyond those that naturally enter the ear. While in still further embodiments, two signal processors may be used. One signal processor is used for generating electrical stimulations in conjunction with a second speech processor used for producing acoustic stimulations. There is utilitarian value with respect to synchronizing the output of the two processors.

As shown in FIGS. 1B and 1C, a receiver in the ear 250 is connected to the signal processor through cable 252. Receiver in the ear 250 includes a housing 256, which may be a molding shaped to the recipient. Inside receiver in the ear 250 there is provided a capacitor 258, receiver 260 and protector 262. Also, there may be a vent shaft 264 (in some embodiments, this vent shaft is not included). Receiver in the ear may be an in-the-ear (ITE) or completely-in-canal (CIC) configuration.

Also, FIG. 1B shows a removable battery 270 directly attached to the body/spine of the BTE device. As seen, the BTE device in some embodiments control buttons 274. In addition, the BTE may house a power source (not shown), e.g., zinc-air batteries. The BTE device may have an indicator light 276 on the earhook to indicate operational status of signal processor. Examples of status indications include a flicker when receiving incoming sounds, low rate flashing when power source is low or high rate flashing for other problems.

Returning to FIG. 1A, internal components 244 comprise an internal receiver unit 212, a stimulator unit 226 and an electrode assembly 218. Internal receiver unit 212 comprises an internal transcutaneous transfer coil (not shown), and preferably, a magnet (also not shown) fixed relative to the internal coil. Internal receiver unit 212 and stimulator unit 226 are hermetically sealed within a biocompatible housing. The internal coil receives power and data from external coil 208, as noted above. A cable or lead of electrode assembly 218 extends from stimulator unit 226 to cochlea 232 and terminates in an array 234 of electrodes 236. Electrical signals generated by stimulator unit 226 are applied by electrodes 236 to cochlea 232, thereby stimulating the auditory nerve 238.

In one embodiment, external coil 208 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 212 may be positioned in a recess of the temporal bone adjacent to outer ear 201 of the recipient.

As shown in FIG. 1A, multimodal system 200 is further configured to interoperate with a user interface 280 and an external processor 282 such as a personal computer, workstation, or the like, implementing, for example, a hearing implant fitting system. Although a cable 284 is shown in FIG. 1A between implant 200 and interface 280, a wireless RF communication may also be used along with remote 286.

While FIG. 1A shows a multimodal implant in the ipsilateral ear, in other embodiments of the present invention the multimodal implant may provide stimulation to both ears.

For example, a signal processor may provide electrical stimulation to one ear and provide acoustical stimulation in the other ear.

Figure 2:
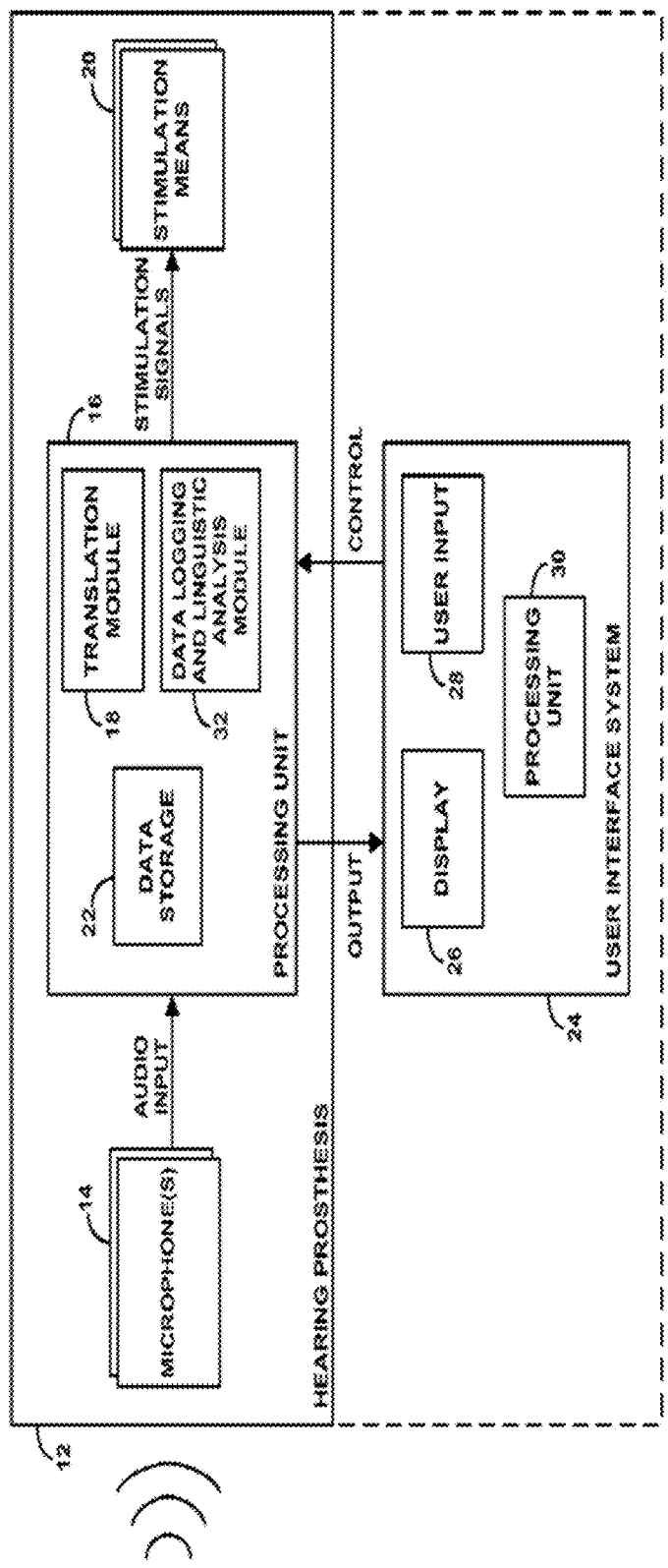
FIG. 2 depicts an exemplary functional diagram of an exemplary hearing prosthesis.

FIG. 2 is a simplified functional block diagram of an exemplary hearing prosthesis 12 operable in accordance with the present disclosure, wherein the features of FIG. 2 can be included in the embodiments of FIGS. 1A-1C. As shown, consistent with the above, the hearing prosthesis 12 generally includes one or more microphones (microphone inputs) 14 for receiving audio input representing an audio environment of the prosthesis recipient, a processing unit 16 having a translation module 18 for translating a representation of the received audio input into stimulation signals, and a stimulator (one or more stimulation outputs) 20 for stimulating the physiological system of the recipient in accordance with the stimulation signals and thus in accordance with the received audio input. This exemplary hearing prosthesis of FIG. 2 can represent any of various types of hearing prosthesis, including but not limited to those discussed above, and the components shown may accordingly take various forms. The example of FIG. 2 can correspond to other types of hearing prosthesis, such as, by way of example, an acoustic hearing aid, where, for example, the translation module 18 may include an amplifier that amplifies the received audio input, and the stimulator 20 may include a speaker arranged to deliver the amplified audio into the recipient's ear. As another example, if the hearing prosthesis is a vibration-based hearing device, the translation module 18 may function to generate electrical signals corresponding with the received audio input, and the stimulator 20 may include a transducer that delivers vibrations to the recipient in accordance with those electrical stimulation signals. And as yet another example, if the hearing prosthesis is a cochlear implant, the translation module 18 may similarly generate electrical signals corresponding with the received audio input, and the stimulator 20 may include an array of electrodes that deliver the stimulation signals to the recipient's cochlea. Other examples exist.

In practice, the processing unit 16 may be arranged to operate on a digitized representation of the received audio input as established by analog-to-digital conversion circuitry in the processing unit, microphone(s) or one or more other components of the prosthesis. As such, the processing unit 16 may include data storage (e.g., magnetic, optical or flash storage) 22 for holding a digital bit stream representing the received audio and for holding associated data. Further, the processing unit 16 may include a digital signal processor, and the translation module 18 may be a function of the digital signal processor, arranged to analyze the digitized audio and to produce corresponding stimulation signals or associated output. Alternatively or additionally, the processing unit may include one or more general purpose processors (e.g., microprocessors), and the translation module 18 may include a set of program instructions stored in the data storage 322 and executable by the processor(s) to analyze the digitized audio and to produce the corresponding stimulation signals or associated output.

As further shown, the exemplary hearing prosthesis 12 includes or is coupled with a user interface system 24 through which the recipient or others (e.g., a clinician) may control operation of the prosthesis and view various settings and other output of the prosthesis. In practice, for instance, the user interface system 24 may include one or more components internal to or otherwise integrated with the prosthesis. Further, the user interface system 24 may include one or more components external to the prosthesis, and the prosthesis may include a communication interface arranged to communicate with those components through a wireless and/or wired link of any type now known or later developed. In a representative arrangement, the user interface system 22 may include one or more user interface components that enable a user to interact with the hearing prosthesis. As shown by way of example, the user interface components may include a display screen 26 and/or one or more input mechanisms 28 such as a touch-sensitive display surface, a keypad, individual buttons, or the like. These user interface components may communicate with the processing unit 16 of the hearing prosthesis in much the same way that conventional user interface components interact with the host processor of a personal computer. Alternatively, the user interface system 24 may include one or more standalone computing devices such as a personal computer, mobile phone, tablet, handheld remote control, or the like, and may further include its own processing unit 30 that interacts with the hearing prosthesis and may be arranged to carry out various other functions.

In accordance with an exemplary embodiment, the exemplary hearing prosthesis 12 can additionally function to log and output data regarding the received audio input. In particular, the hearing prosthesis may analyze the received audio input so as to identify (sometimes referred to herein as "determine") one or more biomarkers in the recipient's audio environment and can output data representing the identified/determined one or more biomarkers. In an exemplary embodiment, the biomarkers are linguistic characteristics of the recipient's speech. Further, the hearing prosthesis may use its stimulation mode as a basis to generate this data, such as by determining and logging biomarkers just with respect to the audio input received while the hearing prosthesis is in the stimulation-on mode, or by separately recording/identifying, etc., (i) or more biomarkers in the audio input received at times when the hearing prosthesis was in the stimulation-on and (ii) or more biomarkers in the audio input received at times when the hearing prosthesis was in the stimulation-off mode. That is, any mode in which the hearing prosthesis is in can be used to identify/determine the biomarkers. As will be detailed below, other devices and systems can be used to identify/determine the biomarkers.

It is also noted that while the embodiments detailed herein are often made in reference to a hearing prosthesis that includes a sound capture device located external to the recipient, in some alternate embodiments, the teachings detailed herein can be applicable to the so-called "invisible hearing," where, for example, and implanted microphone is utilized with a fully implanted cochlear implant and/or a fully implanted middle ear implant and/or a fully implanted bone conduction device, etc.

The hearing prosthesis may then output logged data from time to time for external analysis, such as for external determination and reporting of linguistic characteristics in the recipient's audio environment. For instance, the user interface system 24 may periodically poll the hearing prosthesis to obtain from the prosthesis the latest biomarkers logged by the prosthesis, such as the latest logged linguistic characteristics corresponding with stimulation-on mode and the latest logged linguistic characteristics corresponding with stimulation-off mode. And the user interface system 24 may process that data and provide a graphical user interface that depicts a comparison of the logged linguistic characteristics (possibly per stimulation mode) over time.

As shown in FIG. 2, the processing unit 16 of the exemplary hearing prosthesis 12 includes a data logging and biomarker module 32, identified as data logging and linguistic analysis (DLLA) module 32 for carrying out some or all of these added functions. This DLLA module 32 may be integrated in whole or in part with the translation module 18, such as by making use of some of the same components of the hearing prosthesis as the translation module 18. Further, as with the translation module, this DLLA module may be provided in various forms. For instance, the DLLA module may be provided as a function of a digital signal processor, or as a set of program instructions stored in data storage and executable by one or more processors to carry out the data logging and linguistic analysis functions.

In practice, as the processing unit 16 receives audio input representing the audio environment of the recipient, the processing unit module may evaluate the audio input in real-time so as to determine one or more linguistic characteristics in the audio input.

The biomarkers in general and the "linguistic characteristics" in particular that are explored here are characteristics specifically related to language production and reception, and can include more general audio characteristics such as amplitude, frequency, or the like. Examples of linguistic characteristics include, among others, (1) a measure of proportion of time spent by the recipient speaking, (2) a measure of proportion of time spent by the recipient receiving speech from others, (3) a measure of quantity of words spoken by the recipient, (4) a measure of quantity of sentences spoken by the recipient, (5) a measure of quantity of words spoken by one or more people other than the recipient, (6) a measure of quantity of sentences spoken by one or more people other than the recipient, (7) a measure of quantity of conversational turns by the recipient, (8) a measure of length of utterances by the recipient or by others, (9) a measure of quantity of phonetic features produced by the recipient, such as voiced vs. unvoiced speech sounds, vowels versus consonants, or a more specific breakdown of consonant articulation such as plosives, affricatives, fricatives, sibilants, nasal, flap, tap, approximant, lateral, trill, and so forth, including for instance a measure of rate of syllabic or other speech production and/or a measure of phoneme variations created, (10) a measure of quality of speech exposure, such as presentation level and signal to noise ratio of the speech, (11) a measure of words spoken by adult versus words spoken by children, (12) a measure of quantity of conversations engaged in or initiated by the recipient, and (13) indications of whether the speech is shouted or conversational.

By way of example only and not by way of limitation, such biomarkers can include (and may not be mutually exclusive to the above) omissions and/or errors in words or portions of words, detection of patterns in speech (e.g., intonation), speech rate, overlap of the recipient's speech with the speech of others (e.g., turn taking, etc.), the frequency and/or content stresses, phonetic errors, and/or place and manner of articulation. Any biomarker that can enable the teachings detailed herein to be implemented can be utilized in at least some exemplary embodiments.

The processing unit 16 may apply various well known audio analysis techniques, or other techniques now known or later developed, to determine the one or more biomarkers in the audio input and may do so in real-time (e.g., continually or periodically as the hearing prosthesis receives the audio input). For example, the processing unit may apply various well known trainable classifier techniques, such as neural networks, Gaussian Mixture models, Hidden Markov models, and tree classifiers. These techniques can be trained to recognize particular linguistic characteristics such as some of those noted above. For instance, a tree classifier can be used to determine the presence of speech in audio input. Further, various ones of these techniques can be trained to recognize segments or quiet spaces between words, and to recognize the difference between male and female voices. Moreover, these techniques could be scaled in order of complexity based on the extent of available computation power.

Implementation of a classifier can be executed utilizing several stages of processing. In a two-stage classifier, for instance, the first stage is used to extract information from a raw signal representing the received audio input provided by the one or more microphones. This information can be anything from the raw audio signal itself, to specific features of the audio signal ("feature extraction"), such as pitch, modulation depth, etc. The second stage then uses this information to identify one or more probability estimates for a current class at issue.

In order for the second stage of this technique to work, there is utilitarian value in training the second stage. Training involves, by way of example, collecting a pre-recorded set of example outputs ("training data") from the system to be classified, representing what engineers or others agree is a highest probability classification from a closed set of possible classes to be classified, such as audio of music or speech recorded through the prosthesis microphones. To train the second stage, this training data is then processed by the first stage feature extraction methods, and these first stage features are noted and matched to the agreed class. Through this design process, a pattern will ultimately be evident among all the feature values versus the agreed class collected. For example, all of the speech samples might have a modulation depth above 0.5, while all noise signals might be below 0.2. Well-known algorithms may then be applied to help sort this data and to decide how best to implement the second stage classifier using the feature extraction and training data available. For example, in a tree classifier, a decision tree may be used to implement an efficient method for the second stage. Nodes of the tree may thus have values such as "is modulation depth<0.5" as conditions for which direction to branch. And each path may end at a highest probability class decision (such as a classification as music, speech, etc.)

In applying such a technique to identify linguistic characteristics in the received audio input, the training data may for example contain spoken words and sentences, by male and female speakers of various ages, and perhaps speech specifically by the recipient. Further, the feature extraction stage may contain voiced and unvoiced speech segment detectors, and perhaps a fast moving level measure to track the time between gaps in sentences. A two-stage classifier could then be trained to recognize when a sentence had been spoken, and to distinguish other sounds as not being a sentence.

As still another example, the processing unit may apply various well known speech recognition techniques to detect the extent of speech in the audio input. Those techniques may require significant computational power and may or may not be suitable for real-time analysis by prosthesis processing units without the assistance of an external processing unit for instance. However, continued developments in signaling processing technology and speech recognition algorithms may make actual speech recognition, including speaker recognition, more suitable for implementation by the processing unit of a hearing prosthesis.

Further, in terms of determining whether identified speech is speech of the recipient or speech of another person in the recipient's environment, the processing unit may take various factors into consideration. For instance, the processing unit may take into account loudness and frequency range of the speech, possibly by way of comparison with test samples of the recipient's own voice. In addition, if the prosthesis has multiple microphones for receiving the audio input and the processing unit receives separate audio input from each microphone, the processing unit may use those separate inputs to differentiate between (i) the recipient's speech as may be picked up by a microphone positioned to best pick up speech coming from the recipient and (ii) others' speech as may be picked up by a microphone positioned to best pick up speech directed at the recipient.

Moreover, to facilitate carrying out this analysis in real-time, the processing unit may limit its analysis to identify key parameters as proxies for more complex linguistic characteristics or may generally estimate various ones of the linguistic characteristics rather than striving to determine them exactly. For instance, rather than working to determine an exact count of words spoken by the recipient or spoke by others in the recipient's environment, the processing unit may determine an approximate count. Such an approximation may be clinically relevant, as it may facilitate general comparisons between extents of speech to which the recipient is exposed. For example, if the processing unit determines that the recipient is exposed to approximately 400 words one day and approximately 600 words the next day, that 50% estimated increase may be key to evaluating the recipient's speech exposure.

Optimally, as the processing unit receives the audio input, the processing unit may record various associated data in data storage 22. Further, the processing unit may output the data in real-time or at some later time to the user interface system 24.

By way of example, as the processing unit determines the one or more linguistic characteristics of the recipient's audio environment, the processing unit may record those characteristics in correspondence with indications of whether the hearing prosthesis is in the stimulation-on mode or is rather in the stimulation-off mode. For instance, the processing unit may keep track over time of the rate or number of words, sentences, or the like, in the audio input at times when the prosthesis is in the stimulation-on mode and may separately keep track over time of the rate or number of words, sentences, or the like, in the audio input at times when the prosthesis is in the stimulation-off mode. And the processing unit may output data representing these metrics, possibly in real-time as the processing unit generates the metrics. For instance, as noted above, the user interface system 24 may periodically poll the prosthesis for such metrics and may receive and timestamp the metrics, to facilitate determining and presenting changes in the metrics over time. Alternatively, the processing unit may push the data periodically to the user interface system or otherwise output the data.

In practice, the processing unit can provide this and other data to the user interface system 24 in various forms for presentation to a user such as the recipient or a clinician. For example, the processing unit may provide the data in raw form, as one or more lists of metrics and associated values, such as a list of metrics corresponding with stimulation-on mode and a separate list of metrics corresponding with stimulation-off mode. As another example, the processing unit may structure the data as graphs and other charts more readily understandable at quick glance. For instance, rather than or in addition to listing the number of words spoken by the recipient on each of various days, the processing unit may provide a graph that shows change in number of words spoke per day or per other unit of time, which could then be analyzed in terms of the recipient's environment. In practice, the processing unit may generate these graphs as graphical user interfaces suitable for presentation by display 26.

In an alternative arrangement, note also that some of this analysis and presentation could be done by an external processing unit, such as processing unit 30 of an external computing device. In line with the discussion above, for instance, the processing unit 16 of the hearing prosthesis may record separate sets of linguistic characteristics corresponding with stimulation-on mode and stimulation-off mode, and processing unit 16 may periodically or otherwise from time to time provide the latest such sets of data to the processing unit 30 of the external computing device. Upon receipt of such data, processing unit 30 may then timestamp each received set of data with an indication of the current day, time of day, or the like. And processing unit 30 of the external computing device may then analyze the data to determine one or more linguistic characteristics in the audio, again possibly in correspondence with the stimulation mode of the prosthesis, and may similarly present output representing that information, such a depictions of changes in linguistic characteristics in the recipient's audio environment over time.

Figure 3:
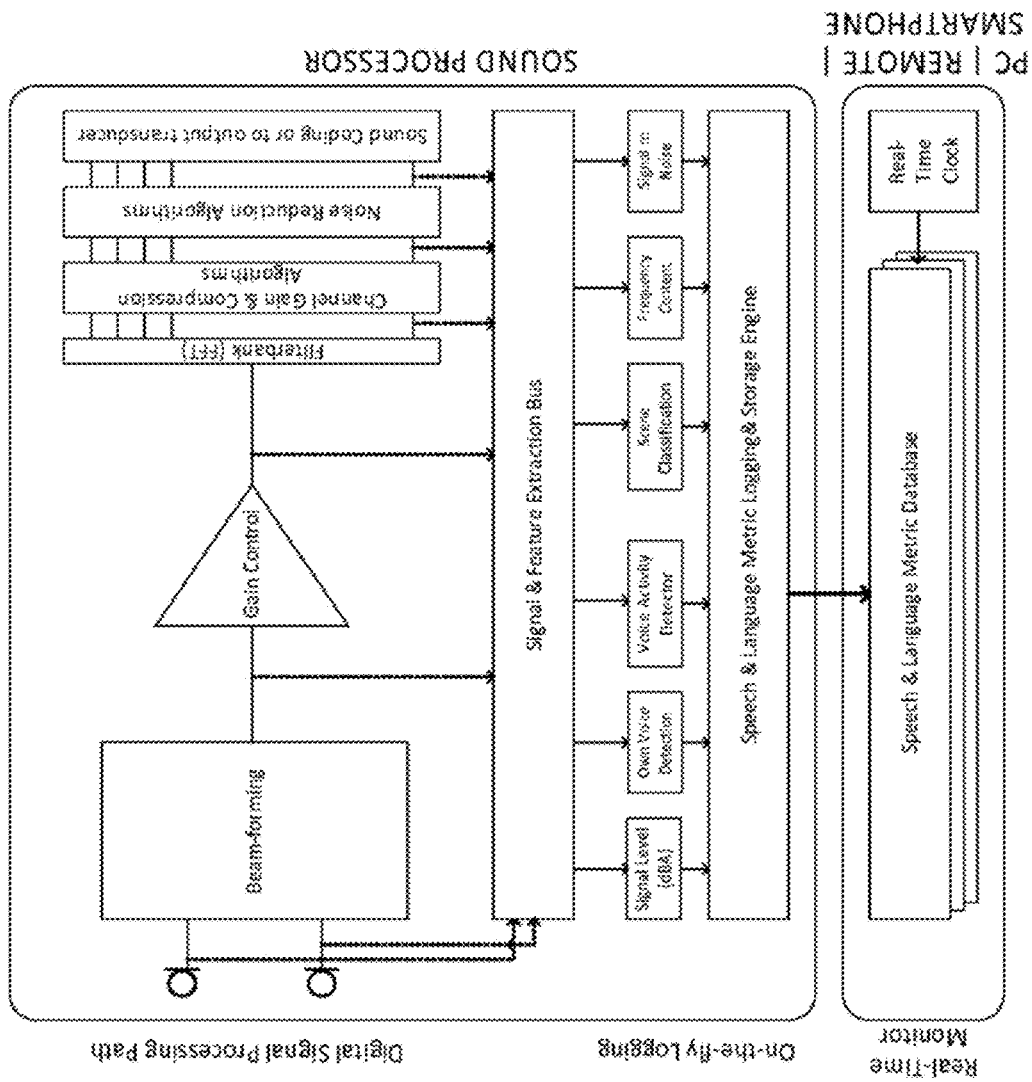
FIG. 3 depicts an exemplary functional diagram of an exemplary processing unit according to an exemplary embodiment.

FIG. 3 is a block diagram depicting more specifically various components that may be included in a representative processing unit 16 and user interface system 24 in accordance with the present disclosure. In particular, FIG. 3 depicts processing unit 16 as a sound processor and user interface system 24 as a real-time monitor, such as a PC, smartphone, and/or remote control. The figure depicts on the sound processor a representative signal processing path for core hearing therapy. Further, the figure depicts extraction of certain metrics from various signal processing blocks, and forwarding of those metrics to a logging engine. The logging engine may then function to categorize the metrics, establish linguistic characterizations, and log the characterizations such as by incrementing counts of particular linguistic characterizations (e.g., number of words spoken by the recipient, number of words spoken by others, etc.), in correspondence with stimulation mode as discussed above. And the real-time monitor is then connected to the sound processor so as to read the stored logs, such as by periodically polling for the latest logged data. And the auxiliary device may timestamp and that data for comparison and trending, such as to determine and present indications of changes over time (e.g., one week versus the last, one month versus the last, etc.) in linguistic characteristics in the recipient's environment.

In view of the above, it is to be understood that in an exemplary embodiment, there is a body worn or implantable hearing prosthesis, such as by way of example only and not by way of limitation, a cochlear implant, a conventional hearing aid, a bone conduction device, a middle ear implant, etc., comprising a device configured to capture an audio environment of a recipient and evoke a hearing percept based at least in part on the captured audio environment. It is noted that in an exemplary embodiment, this can be a multimodal hearing prostheses, such as that depicted in FIGS. 1A-1C above. In an exemplary embodiment, this device can be the assembly comprising a microphone and a cochlear electrode array, a vibrator, a speaker, etc., depending on the type of hearing prostheses. In an exemplary embodiment, the hearing prosthesis is configured to identify, based on the captured audio environment, one or more biomarkers present in the audio environment indicative of the recipient's ability to hear. In an exemplary embodiment, the hearing prosthesis utilizes a configuration corresponding to that of FIGS. 2 and 3 detailed above to identify, based on the captured audio environment, the one or more biomarkers. In an exemplary embodiment, the hearing prosthesis utilizes a configuration corresponding to that of FIGS. 2 and 3 detailed above to execute one or more of the method actions detailed herein.

Figure 4:
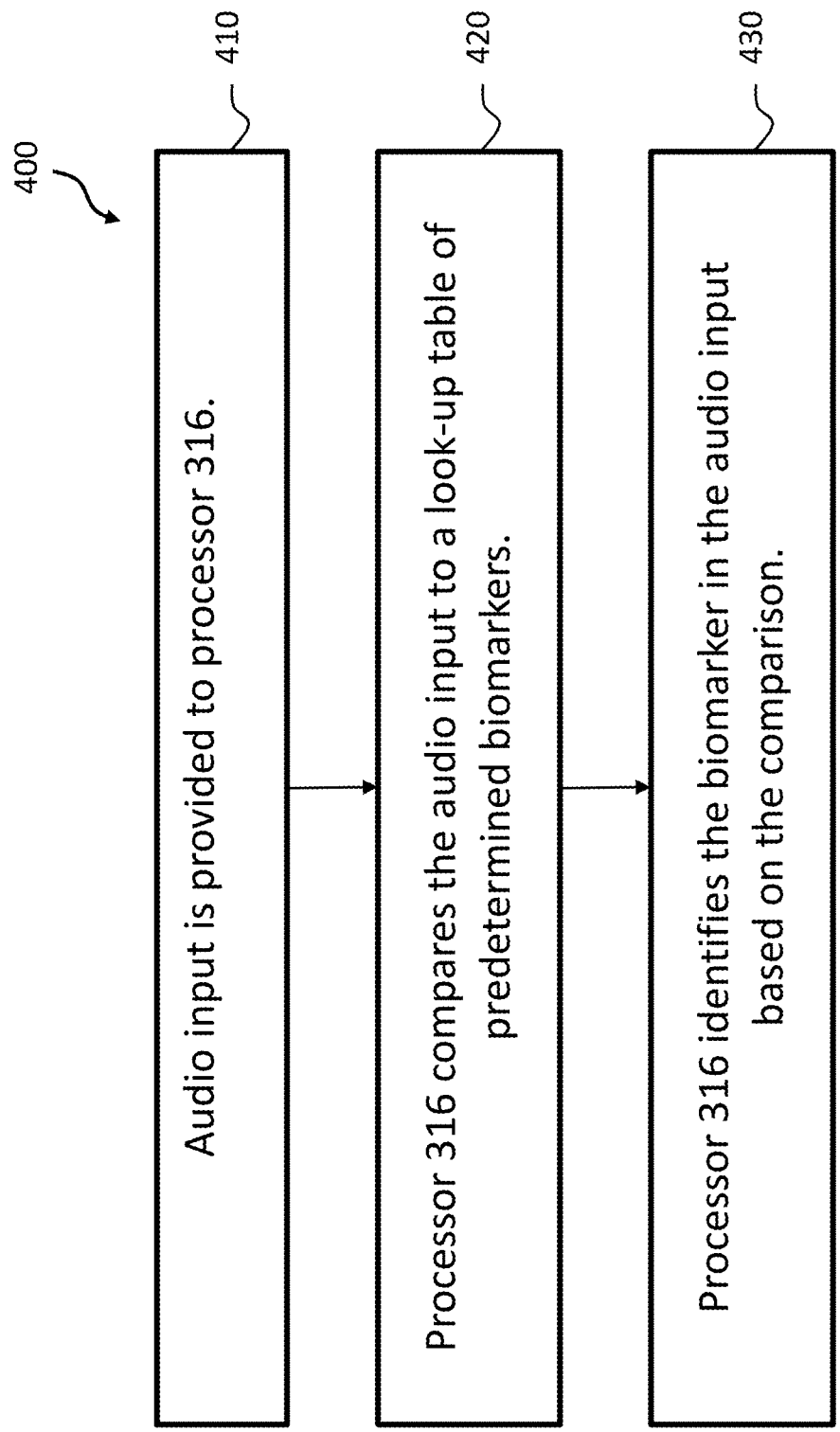
FIG. 4 depicts an exemplary algorithm utilized by the processor of FIG. 2 in an exemplary embodiment.

By way of example only and not by way of limitation, the processing unit 16 can be configured to identify the one or more biomarkers in accordance with the teachings detailed above. In an exemplary embodiment, the audio input is analyzed by comparing the audio input to a lookup table of predetermined biomarkers, and identifying the biomarkers from the lookup table. FIG. 4 depicts an exemplary flowchart for an exemplary algorithm utilized by processor 16. More particularly, FIG. 4 depicts an algorithm 400 includes method action 410, which includes providing the audio input to processor 16. Algorithm 400 further includes method action 420, which includes utilizing processor 16 to compare the audio input to a lookup table of predetermined biomarkers. In method action 430, based on this identification, the processor 16 identifies the biomarker in the audio input.

In at least some embodiments, the biomarkers utilized herein are biomarkers that are known or at least suspected to be biomarkers that have some correlation with the ability of the recipient to hear. In this regard, in at least some exemplary embodiments of the teachings detailed herein, the biomarkers are anchored to some known reference that is indicative of whether or not the biomarker indicates the recipient can hear adequately, etc. Also, as will be described in greater detail below, a recipient-centric approach can utilize a regime where biomarkers are anchored against a so-called "nearest neighbor" type approach (e.g., people like the recipient would be expected to have certain speech biomarkers at the time that commencement of utilization of the hearing prosthesis occurs, and would have certain speech biomarkers 3 months out, and certain speech biomarkers 6 months out, 1 year out, 18 months out, 2 years out, 3 years out, etc.). Any of the disclosed utilization of biomarkers detailed herein can utilize this approach.

In an exemplary embodiment, the audio environment can include the speech of the recipient and/or the speech of others, whether in a conversational form or from a fixed source, such as from a radio or television, etc. In some embodiments, the audio environment can further include any other aspects that can enable the teachings detailed herein and/or variations thereof.

It is noted that in other alternative embodiments, alternatively and/or in addition to the use of the lookup table, other systems of identifying the biomarkers can be utilized. Any arrangement that can permit such can be utilized in at least some exemplary embodiments.

To be clear, in an exemplary embodiment, the hearing prosthesis represented by FIG. 2 can be configured in general, and the processor 16 can be provided with software and/or firmware in particular, to enable the processor 16 to identify, based on the audio input provided thereto, the one or more biomarkers present in the audio environment.

As noted above, the identified biomarkers are biomarkers that are indicative of the recipient's ability to hear. These can be any biomarker and/or linguistic characteristics that are indicative of the recipient's ability to hear, some more detailed examples will be described below. However, it is briefly noted that in at least some exemplary embodiments, at least where the audio environment includes speech of the recipient, the one or more biomarkers are linguistic characteristics of the speech of the recipient and the hearing prosthesis is configured to identify the linguistic characteristics as such. In this regard, the action of identifying the one or more biomarkers includes evaluating the speech of the recipient by acoustically analyzing patterns in speech production of the recipient. In an exemplary embodiment, where a pattern in the speech production indicates difficulty of the recipient in producing the "s" or "sh" sounds, this linguistic characteristic can be indicative of the recipient's ability to hear high frequencies (which is thus difficulty with hearing high frequencies).

More generally, embodiments detailed herein and/or variations thereof can be directed towards utilizing speech production of a recipient of a hearing prosthesis to provide an indicator of speech perception, which is correlated to an ability of a recipient to hear. Typically, recipients of hearing prostheses have a mentally ingrained pronunciation self-correction method whereby pronunciation is modified to match that of the pronunciation they hear (perceive they hear). For example, in cochlear implant recipients, the spoken pronunciation can be skewed by the recipient hearing pronunciation differently to what a normal hearer might hear. This skewing of pronunciation, for example, could be due to a level imbalance of low and high frequencies. Because the recipient might be hearing high frequencies at a lower level than the low frequencies, the recipient can have a lower level when the recipient produces high frequencies. Thus, by analyzing the user speech, biomarkers can be detected or otherwise identified that are indicative of the recipient's ability to hear.

It is noted that other speech production "problems" can be utilized in some embodiments, such as, by way of example only and not by way of limitation, intonation, stress, length and/or fundamental frequency characteristics. Any one or more of these can be a biomarker utilized by the prosthesis of FIG. 3 or the other systems detailed herein (or the methods detailed herein) or other types of systems that can enable the teachings detailed herein. Other biomarkers can be utilized as well. Any biomarker that can enable the teachings detailed herein and/or variations thereof can be utilized in at least some exemplary embodiments. Thus, in an exemplary embodiment, the prosthesis of FIG. 2 is configured to extract acoustic biomarkers present in the recipient's own voice that are captured during prosthesis operation (whether that be the stimulation on-mode or off-mode). As will be detailed below, such can be used to manage the clinical care of the individual (whether such be obtained from the hearing prosthesis or another system, such as a remote microphone or a smartphone, etc.—more on this below). It is noted that in at least some exemplary embodiments, the extracted biomarkers are extracted from the recipient speech, whether such is an adult or a child (adolescent, pre-adolescent, infant, toddler, etc.)

Figure 5:
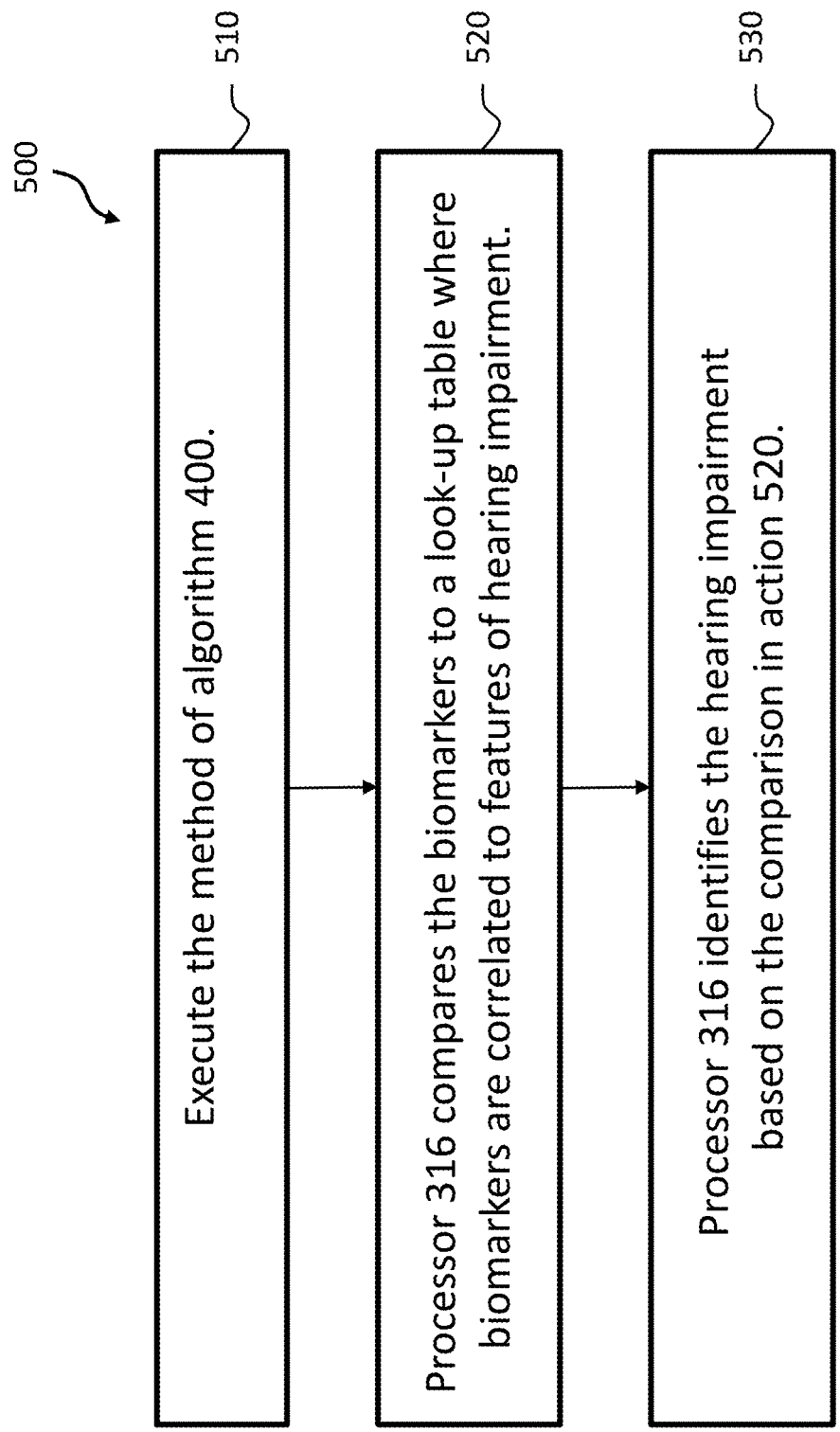
FIG. 5 depicts an exemplary algorithm utilized by the processor of FIG. 2 in an exemplary embodiment.

In an exemplary embodiment, the hearing prosthesis of FIG. 2 (or other system in some alternate embodiments, such as a remote personal computer, a smart phone utilizing or otherwise having a pertinent app thereon, a remote microphone in signal communication with a remote analysis center, etc.—more on this below) can be configured to evaluate the one or more biomarkers and develop data indicative of the recipient's ability to hear. By way of example only, FIG. 5 presents an exemplary algorithm 500 which represents an exemplary method of evaluating one or more biomarkers in developing data indicative of the recipient's ability to hear. Particularly, there is method action 510, which includes executing the method of algorithm 400. Method action 520 includes utilizing processor 16 to compare the biomarkers identified in method action 510, a lookup table where the biomarkers are correlated to features of the hearing impairment. By way of example only and not by way of limitation, in an exemplary embodiment, where the biomarker indicative of the recipient's difficulty in pronouncing the "s" sound is identified in method action 510, method action 520 can result in comparing this biomarker to the lookup table. Method action 530 includes utilizing processor 16 to identify the hearing impairment based on the comparison in action 520. By way of example only and not by way of limitation, such as where the biomarker is indicative of the recipient's ability in pronouncing the "s," sound, the comparison of this biomarker to the lookup table could result in a feature of hearing impairment corresponding to difficulty in hearing high pitched/high-frequency sounds. Thus, in an exemplary embodiment, the results of method 530 can be the identification of the hearing impairment corresponding to difficulty in hearing high pitch sounds. In an exemplary embodiment, the processor 16 can develop data indicative of the recipient's inability or otherwise difficulty in hearing high pitched sounds. This can correspond to outputting a signal from the processor 16 to the data storage unit 322, with signal is indicative of the recipient's ability to hear (e.g., difficulty in hearing high pitched sounds). The data storage unit 322 can store this information for subsequent downloading and/or uploading further analysis as will be described in greater detail below.

Figure 6:
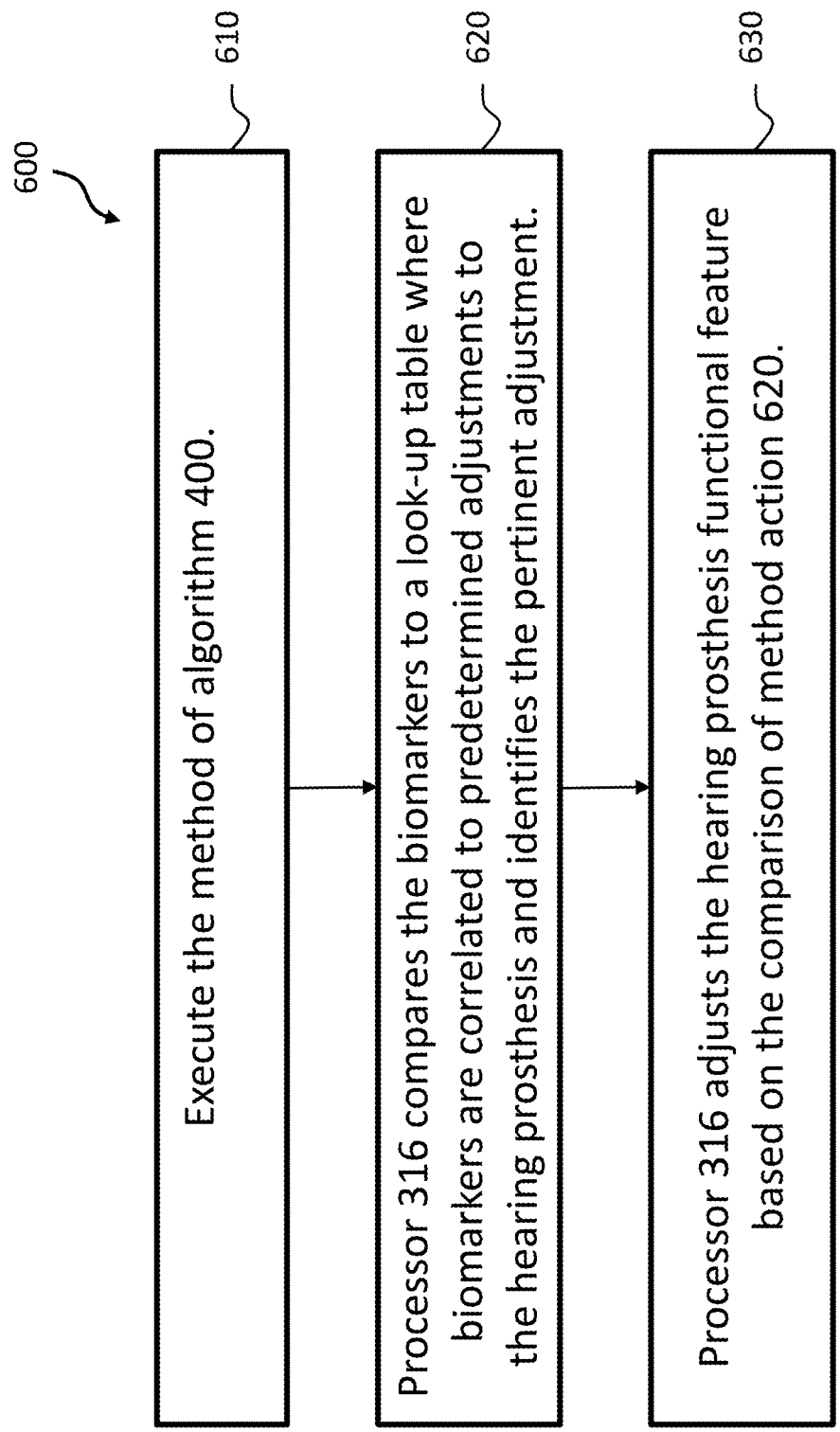
FIG. 6 depicts an exemplary algorithm utilized by the processor of FIG. 2 in an exemplary embodiment.

Alternatively, or in addition to this, in an exemplary embodiment, the hearing prosthesis can be configured to automatically adjust a feature of the hearing prosthesis based on this identification. By way of example only and not by way of limitation, in an exemplary embodiment, for the identification of the biomarker corresponds to the difficulty of the recipient to pronounce the "s" sound, the hearing prosthesis can automatically increase the gain for the higher frequencies at least relative to that which is the case for the other frequencies. To this end, FIG. 6 depicts an exemplary algorithm 600 for an exemplary method utilized by an exemplary hearing prosthesis. Algorithm 600 includes method action 610, which includes executing the method of algorithm 400. Algorithm 600 further includes method action 620, which includes utilizing processor 16 to compare the biomarkers to a lookup table where the biomarkers are correlated to predetermine adjustments to the hearing prostheses and identifies the pertinent adjustments to the hearing prosthesis based on the comparison. Algorithm 600 further includes method action 630, which includes utilizing processor 16 to adjust the hearing prosthesis functional feature based on the comparison of method action 620. Here, in an exemplary embodiment, where, in the case of the identified biomarker corresponding to the recipient's difficulty in pronouncing the "s" sound, method action 620 results in the identification of an adjustment to the hearing prosthesis corresponding to an increasing gain of the higher frequencies of the hearing prosthesis, and method action 630 includes adjusting the hearing prosthesis such that the gain is higher for those frequencies.

It can be seen that the algorithm of FIG. 6 "skips" the action of identifying or otherwise development of data indicative of the recipient's ability to hear. In this regard, in at least some exemplary embodiments, all that is utilized is the identified biomarker identified in the method of algorithm 400. That said, in an alternate embodiment, alternatively, or in addition to this, the method of algorithm 500 can be executed at action 610 instead of the method of algorithm 400, and at method action 620, the processor 16 compares the resulting developed data indicative of the recipient's ability to hear to a lookup table where the various abilities of the recipient to hear are correlated to predetermine adjustments to the hearing prosthesis. In method 620, based on the comparison, an identification of the pertinent adjustment is developed. Thus, it can be seen that the algorithm of FIG. 6 as presented "skips a step." Any device, system, or method of implementing the teachings detailed herein to adjust a hearing prosthesis based on the recipient's speech in general, and biomarkers of the recipient speed, can be utilized in at least some exemplary embodiments.

In a more specific exemplary scenario resulting from the execution of the method of the algorithm 600, such as where the prosthesis is a multimodal hearing prosthesis, the biomarker identified at method action 610 can correspond to a biomarker that indicates a frequency threshold of the recipient's hearing, or at least a frequency threshold of the recipients hearing impairment, where the recipient can still hear frequencies above this threshold, but with more difficulty (noticeable difficulty) than that which is the case below. Thus, in an exemplary embodiment, at method action 620, processor 16 compares this biomarker to a lookup table where the biomarker is correlated to a predetermined crossover point of the multimodal hearing prosthesis (the point at which the prosthesis stimulates utilizing electric hearing as opposed to acoustic hearing, for example), and identifies an adjustment to the crossover point based on the comparison. For example, if in the totality of the circumstances, the prosthesis determines that the recipient is having difficulty hearing above 1,250 Hz, method action 620 results in the selection of an adjustment to the hearing prosthesis to change the crossover point (likely lower the crossover point) of the hearing prostheses. Thus, at method action 630, the processor 16 adjusts the hearing prosthesis functional feature such that the crossover point between acoustic hearing and electric hearing is at 1,250 Hz (whereas previously, the crossover point could have been 1750 Hz or 1500 Hz, etc.).

Some additional features of the hearing prosthesis vis-à-vis utilizing ambient sound/environmental sound as part of a regime to evaluate the recipient's ability to hear. However, some exemplary methods will first be described in greater detail than that of the above.

Figure 7:
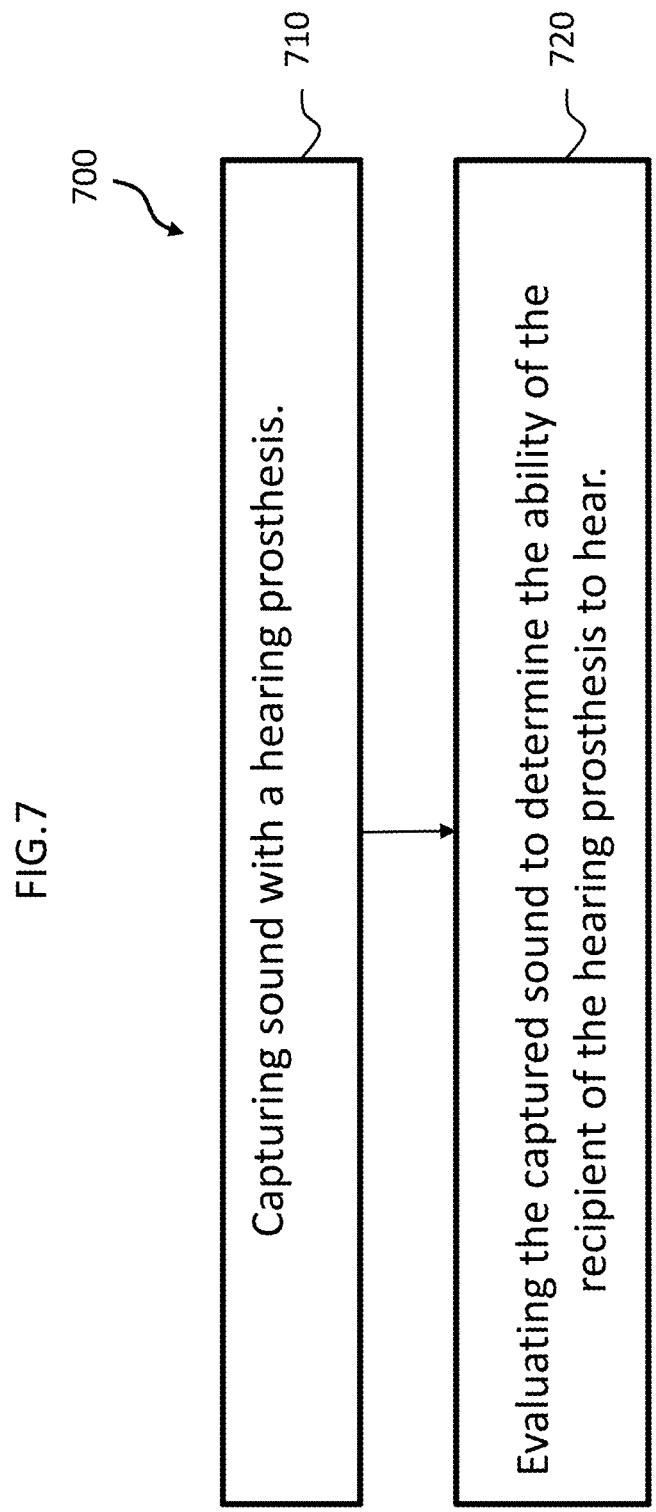
FIG. 7 depicts an exemplary flowchart for an exemplary method according to an exemplary embodiment.

FIG. 7 depicts an exemplary flowchart for an exemplary method, method 700. Method 700 includes method action 710, which includes capturing sound of the hearing prosthesis. In an exemplary embodiment, this can be done utilizing any of the hearing prostheses detailed herein and/or variations thereof, such as those that include a microphone. Method 700 further includes method action 720, which includes evaluating the captured sound to determine the ability of the recipient of the hearing prosthesis to hear. As will be understood, in an exemplary embodiment, when the captured sound includes the sound of the recipient's own voice, such evaluation can include using some or all of the teachings detailed above to evaluate the recipient's ability to hear. By way of example only and not by way of limitation, again utilizing the scenario where the captured sound includes the pronunciation by the recipient of the "s" sound, the hearing prosthesis can evaluate the pronunciation and determine that the recipient is having difficulty hearing high frequencies. This can be accomplished utilizing a modified algorithm according to the teachings detailed above, such as those where the biomarker is compared to a series of biomarkers in a lookup table to determine the hearing impairment of the recipient. That said, in an alternate embodiment, the action of evaluating the captured sound can be performed by another device. By way of example only and not by way of limitation, method 700 can be executed utilizing the microphone of the hearing prosthesis, and the sound captured thereby can be transmitted to a smart phone that includes a app to execute method action 720. Such transmission can occur constantly whenever the microphone is capturing sound or can be more limited, such as only when the hearing prosthesis makes a determination that the recipient is speaking (so as to save battery power and/or processing power). In an exemplary embodiment, the hearing prosthesis can be configured to evaluate the sound and detect or otherwise determine that the recipient is speaking based on the captured sound. Alternatively, the hearing prosthesis can include an accelerometer or the like that can detect or otherwise indicate that the recipient is speaking. Still further, in an exemplary embodiment, a manual device can be utilized by the recipient that activates the transmission only when the recipient wants the transmission to occur. By way of example only and not by way of limitation, the recipient can be trained to activate and deactivate transmission such that the transmission occurs when the recipient is speaking.

Note also that in at least some exemplary embodiments, an onboard recorder of the hearing prosthesis can record the captured sound and periodically provide a transmission to a remote component that executes method action 720. Still further, in an exemplary embodiment, the prosthesis can be configured such that the sound is recorded only when the prosthesis identifies the recipient is speaking, and then periodically provide a transmission to a remote component that analyzes or otherwise executes method action 720. As will be understood, in an exemplary embodiment, in some instances, method action 720 is executed by a machine an automated manner. That said, in some alternate embodiments, the analysis of method action 720 can be executed manually. By way of example, the periodic recordings can be provided via the Internet to a trained audiologist to evaluate the captured sound and make a determination as to the ability of the recipient to hear. Any device, system, and/or method that can enable method 700 to be practiced can be utilized in at least some exemplary embodiments.

In some exemplary embodiments, the hearing prosthesis is configured to evaluate the one or more biomarkers and develop data indicative of the recipient's ability to speak (instead of or in addition to developing data indicative of the recipient's ability to hear). In this regard, there is utilitarian value in capturing the measurement of speech production not just from the point of view of predicting hearing performance, but also from the perspective of tracking how the individual is producing speech on a daily basis and the quality of speech produced, how the speech production is improving over time and/or whether there is a need to intervene by a speech pathologist when consistent errors are observed. In an exemplary embodiment, an exemplary scenario of an intervention can include training the individual to better produce an identified issue with speech production. By way of example only, when an identified "abnormality" with the recipient's own voice is identified (with reference with their expected vocal production trajectory), the identified differences are noted, either by an expert system (person or machine), and upon such noting an auditory verbal training regime focused on the identified problem is implemented. In an exemplary embodiment, the expert system can interact directly with the recipient via a device (computer, smart phone including an application for such purposes, etc.) that addresses the issue using streamed speech, for example, and presents exercises to the recipient requiring feedback from recipient to train out the speech problem. That is, in an exemplary embodiment, instead of or in addition to attempting to improve the recipient's ability to hear, the teachings detailed herein can be applied to improving the recipient's ability to speak. Thus, in an exemplary embodiment, there is a method of training a person to speak instead of or in addition to gauging hearing ability based on speech. In this regard, in practical terms, the clinical outcome of the individual is related at least in part to the individual's ability to perceive sounds and articulate sounds. By way of example, the biomarkers can be utilized to develop a speech therapy, such as by selecting one or more of the speech therapies offered by the American Speech and Language Association (ASHA). Any regime of treating mis-articulation in speech can be utilized, whether such be visual and/or auditory based.

Still further, an exemplary therapy that can be implemented includes instructing the recipient to use, if such exists, the better ear (e.g., the ear to which a conventional hearing aid has been applied, as opposed to the ear in which a cochlear implant has been applied) as a vehicle for delivering training input signals. For example, where a cochlear implant recipient has the implant in one ear and a hearing aid in the other ear, an exemplary embodiment includes an expert system in a component of the device that detects mis-articulation based on the biomarkers of the recipient's speech and recommends to the recipient, via, for example, the smart phone or other interactive device, that the recipient would benefit from a speech therapy program. In this exemplary embodiment, the system of which the implant and the acoustic hearing aid is apart (or just one of the two is a part) "knows" that that the ear with the acoustic hearing aid is performing sufficiently well and determines to stream audio only to the acoustic hearing aid for speech training (to, for example, demonstrate to the recipient "this is what the sound should sound like"), and then streams to the poorer CI ear to provide contrast with the same input.

Figure 8:
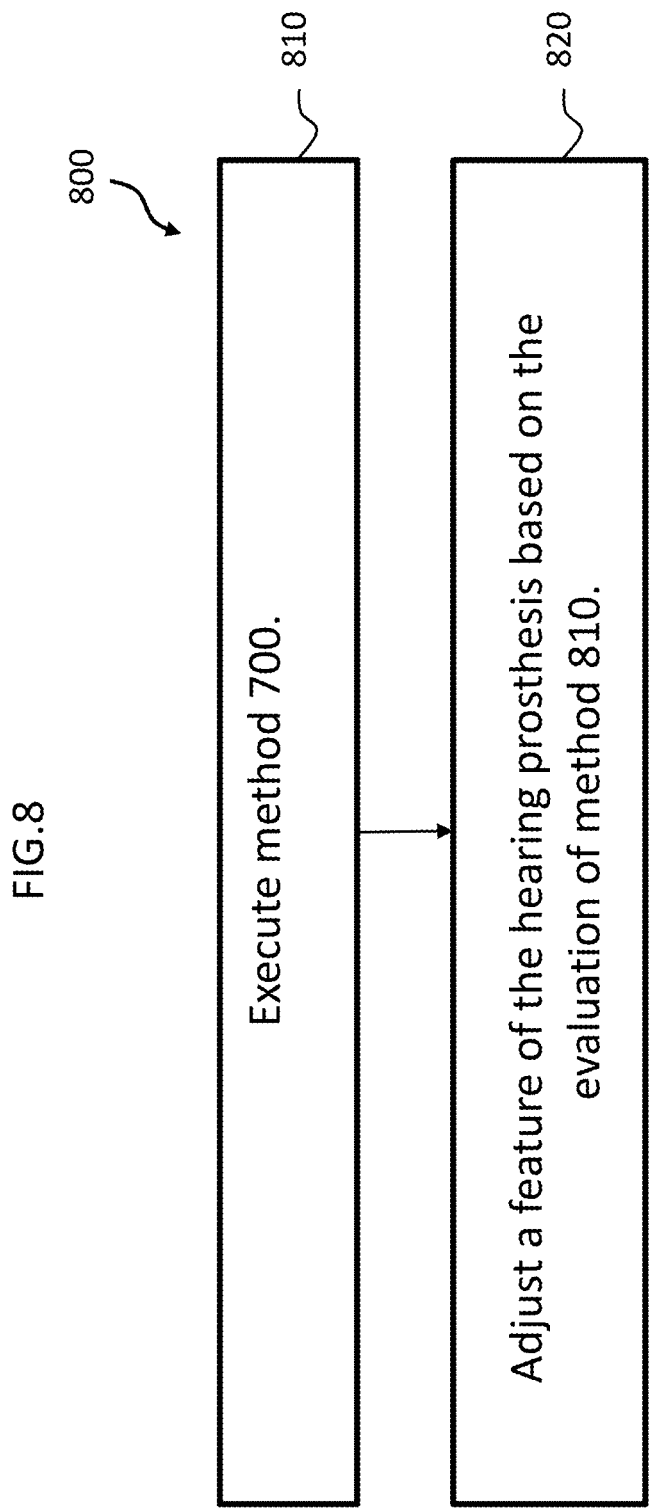
FIG. 8 depicts another exemplary flowchart for another exemplary method according to another exemplary embodiment.

FIG. 8 depicts an exemplary flowchart for an exemplary method, method 800, that includes method action 810, which includes executing method 700, and includes method action 820, which includes adjusting a feature of the hearing prosthesis based on the evaluation of method action 810. Thus, concomitant with the teachings detailed above, in an exemplary embodiment, method action 820 can be executed automatically by the hearing prosthesis. That said, in some alternate embodiments, the action of adjusting the feature of the hearing prosthesis based on the evaluation of method 810 is executed manually or remotely (which could be automatically). In an exemplary embodiment, such can be the case where, for example, the analysis was executed remotely by a healthcare professional such as a trained audiologist. Thus, in an exemplary embodiment, the healthcare professional can evaluate the data and develop a prescription or the like or recommended course of strategy and provides such to the recipient (e.g., via e-mail, telephone call, etc.). Alternatively, and/or in addition to this, the smart phone could provide an indication to the recipient as to how to adjust the hearing prosthesis. Still further, in an exemplary embodiment, the smart phone can automatically remotely adjust the hearing prosthesis. Alternatively, the healthcare professional can adjust the hearing prosthesis remotely, such as via a software update (which could occur automatically on a weekly or monthly basis, etc.). In an exemplary embodiment, such as where for example a personal computer performs evaluation, the evaluation could occur while the recipient is away from the personal computer, and then the prosthesis comes into communication range with the personal computer (e.g., Wi-Fi range, when the recipient connects the prosthesis to the computer, etc.), the computer automatically makes the adjustment to the prosthesis.

Corollary to at least some of the exemplary embodiments just described, in an exemplary embodiment, method action 720 is executed invisibly to the recipient. This is as opposed to a scenario where the recipient is working directly with an audiologist who is attempting to ascertain the ability of the recipient to hear. In an exemplary embodiment, method 700 is executed while the recipient is going about the normal tasks of life where method action 720 is executed in the background, either by the prosthesis or a remote device automatically, or by a remote audiologist, where any of these actions could occur subsequent to the period of time where the recipient is going about the normal actions of life. With respect to normal actions of life, one of these normal actions is engaging in a conversation with another human being. Indeed, in an exemplary embodiment, there is utility with respect to capturing the sound of the sound environment while the recipient is engaging in conversation, as that will at least in some instances results in the recipient speaking.

Additional details of the prosthesis-recipient-remote evaluation system interaction will be described in greater detail below.

Figure 9:
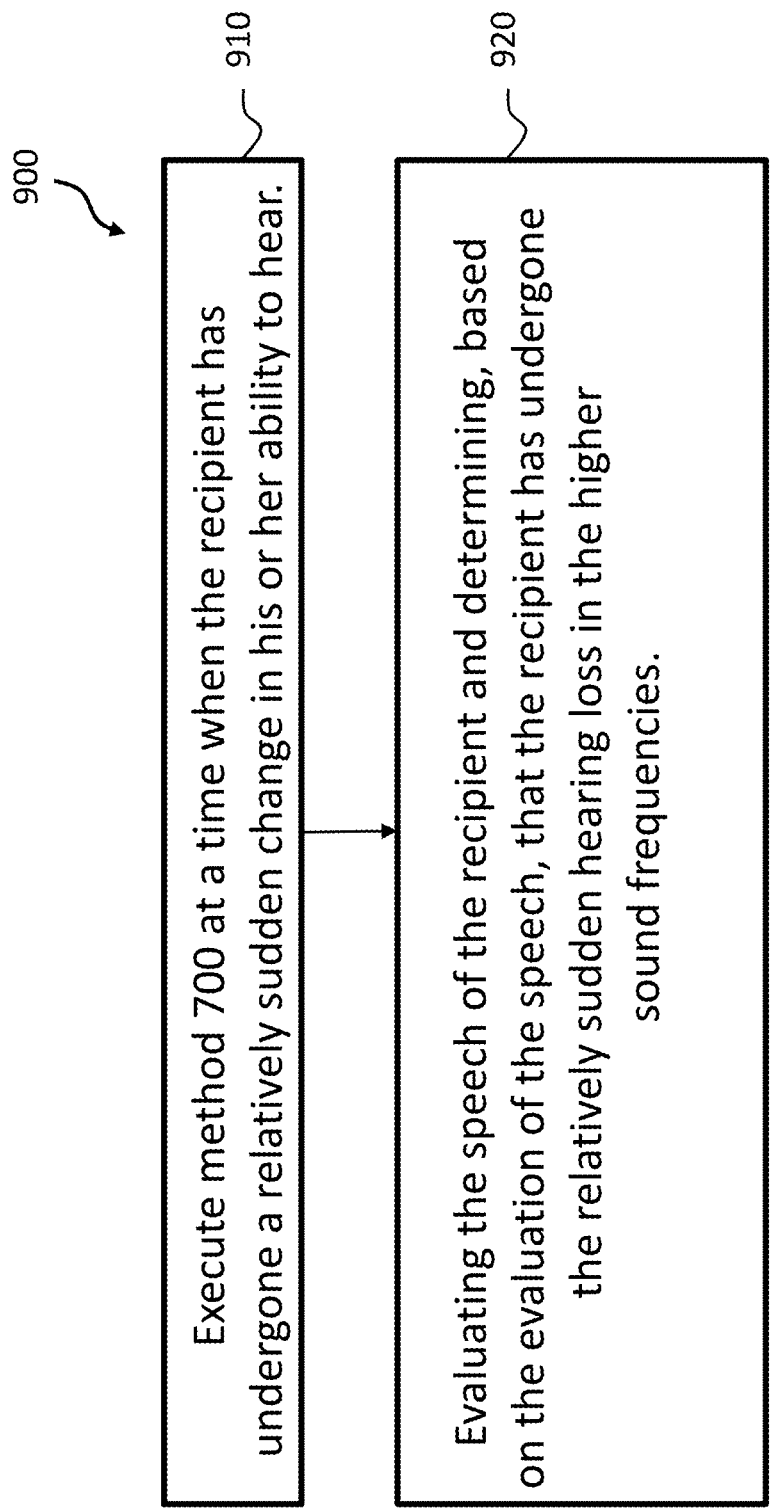
FIG. 9 depicts another exemplary flowchart for another exemplary method according to another exemplary embodiment.

FIG. 9 depicts an exemplary flowchart for an exemplary method 900 according to an exemplary scenario of an exemplary embodiment. Method 900 includes method action 910, which includes executing method 700 at a time when the recipient has undergone a relatively sudden change in his or her ability to hear. In an exemplary embodiment, this relatively sudden change corresponds to relatively sudden hearing loss in the higher sound frequencies. In an exemplary embodiment, the teachings detailed herein are used to identify a statistically significant change has occurred within a time period of less than 9 months, less than 6, months, less than 3 months, less than 2 months, less than 1 month, less than 2 weeks, etc.

Also, it is noted that in some embodiments, because the microphone is also capturing the acoustic environment, the system can be aware that the recipient's listening environment may have also changed and this may explain or account for the variations observed in the biomarkers (e.g. moving from a once quiet environment to a very noisy one for the entire day). In this regard, at least some exemplary embodiments can determine that there is a "justification" for a change in a recipient's ability to hear. In an exemplary embodiment, the system and/or the methods herein could discount such justification. Alternatively, the teachings detailed herein can include weighing the "more difficult to hear in" sound environment to determine that the recipient is hearing well, or otherwise hearing about as well as he or she should be able to hear, in view of the environment/changed environment.

Figure 10:
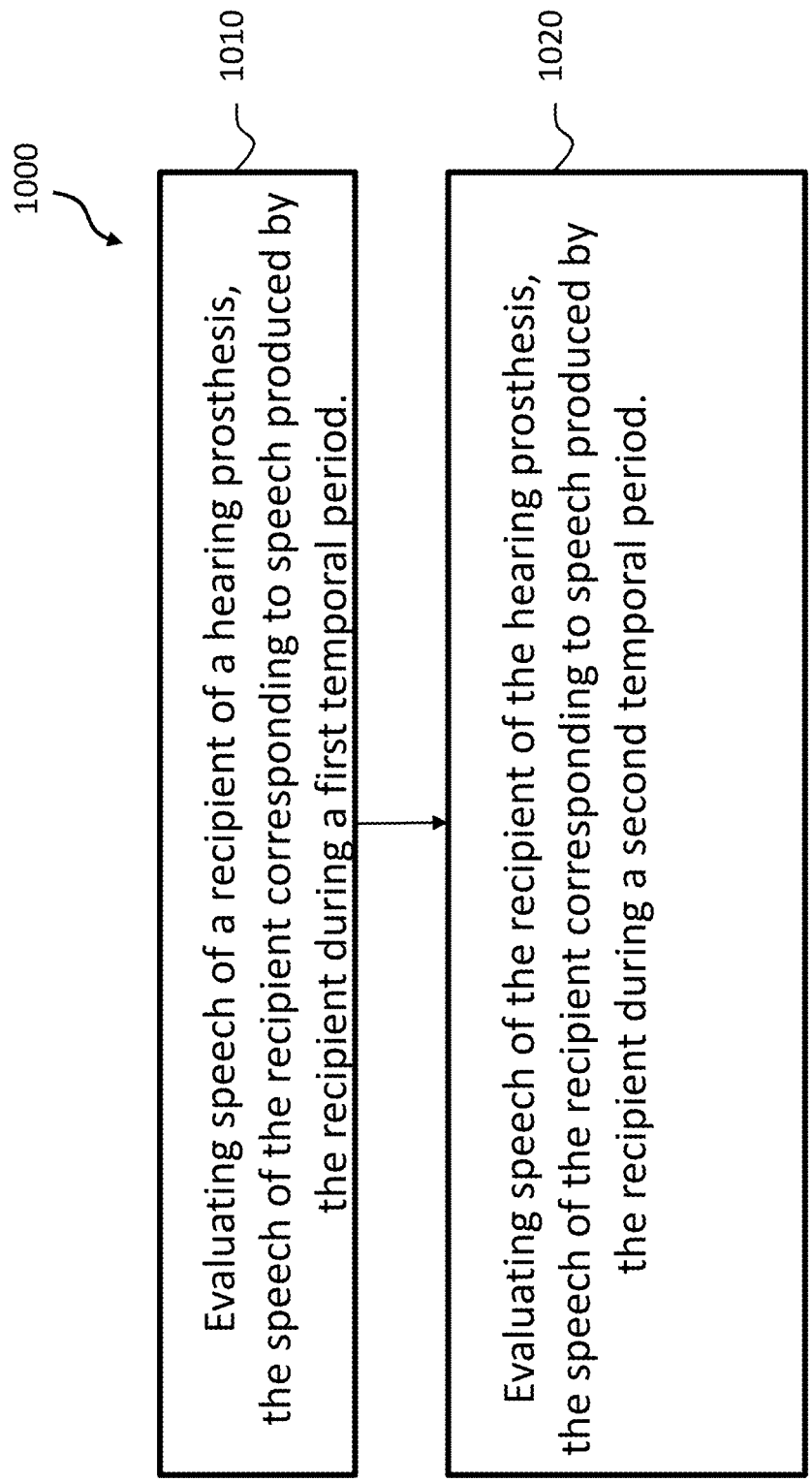
FIG. 10 depicts another exemplary flowchart for another exemplary method according to another exemplary embodiment.

Method 900 further includes method action 920, which includes evaluating the speech of the recipient and determining, based on the evaluation of the speech, that the recipient has undergone the relatively sudden hearing loss in the higher sound frequencies. Again, in an exemplary embodiment where the biomarker corresponding to the recipient's pronunciation of the "s" sound corresponds to a biomarker indicative of the recipient having difficulty hearing high-frequency sounds, an exemplary scenario can occur where the action of evaluating the captured sound indicates that the recipient is not properly pronouncing the "s" sound, at least relative to that which was the case prior to the execution of method action 900, and thus this results in a determination that the recipient has undergone a change in his or her hearing that makes it harder to hear higher frequencies. Consistent with this scenario, FIG. 10 depicts an exemplary flowchart for an exemplary method, which method includes method action 1010, which includes evaluating speech of a recipient of a hearing prosthesis, the speech of the recipient corresponding to speech produced by the recipient during a first temporal period. Method 1000 further includes method action 1020, which includes evaluating speech of the recipient of the hearing prosthesis, the speech of the recipient corresponding to speech produced by the recipient during a second temporal period. In an exemplary embodiment, the second temporal period occurs subsequent to the first temporal period. Thus, concomitant with the aforementioned scenario discussed with reference to FIG. 9, in an exemplary method includes comparing the recipients ability to pronounce the "s" sound during the first temporal period to the recipients ability to pronounce the "s" sound during the second temporal period and determining, based on the comparison, that the recipient has undergone a change in his or her ability to hear. In an exemplary embodiment, this can be done automatically according to the teachings detailed herein (e.g., by hearing prosthesis, by a smart phone, etc.) and/or can be done in a manual manner.

Figure 11:
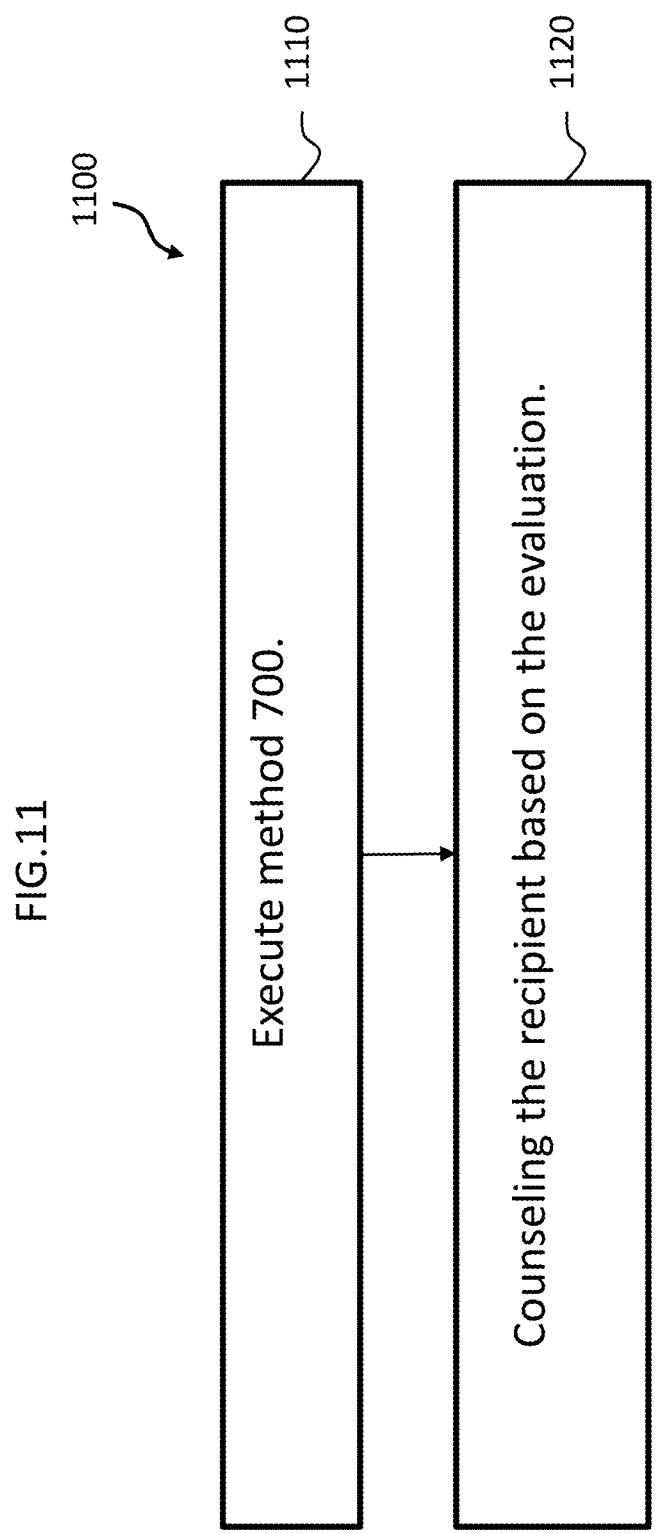
FIG. 11 depicts another exemplary flowchart for another exemplary method according to another exemplary embodiment.
Figure 12:
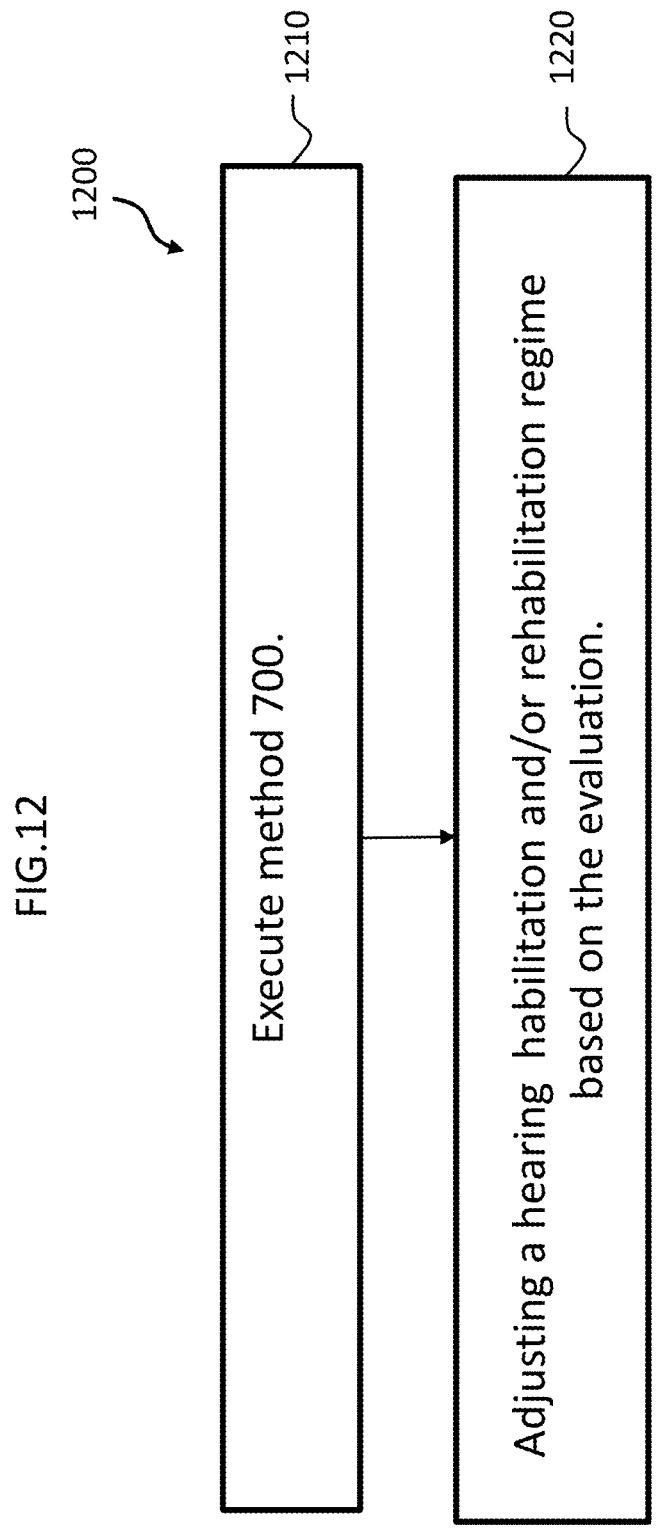
FIG. 12 depicts another exemplary flowchart for another exemplary method according to another exemplary embodiment.

FIG. 11 depicts an exemplary flowchart for another exemplary method according to an exemplary embodiment. Method 1100 of the flowchart of FIG. 11 includes method action 1110, which includes executing method 700. Method 1100 further includes method action 1120, which includes counseling the recipient based on the evaluation of method 1110. In an exemplary embodiment, counseling can include instructing the recipient under what scenarios he or she should pay more attention to people's lips during conversations relative to other times. In an exemplary embodiment, counseling can include instructing the recipient under what scenarios to increase the volume of the hearing prosthesis relative to other times. Some additional counseling scenarios are described below. FIG. 12 depicts an exemplary flowchart for another exemplary method according to an exemplary embodiment. Method 1200 of the flowchart of FIG. 12 includes method action 1210, which includes executing method 700. Method 1200 further includes method action 1220, which includes adjusting a hearing rehabilitation regime based on the evaluation of method action 1110. In an exemplary embodiment, the adjustment of the rehabilitation regime can include instructing the recipient to expose himself or herself to more adult conversation or more precise speakers (e.g., spend more time listening to sports announcers, or news broadcasters, or professional speakers, etc.). In an exemplary embodiment, the adjustment of the rehabilitation regime can include instructing the recipient to listen to more high-frequency sounds.

Other examples of rehabilitation can include by way of example, the provision of either electronic or paper-based rehabilitation materials for use within the clinic and/or home-environment. These materials can also be deployed via a tablet or phone based application, or by computer, or any other mode that enables such provision. Examples of these materials can be game-based activities for practicing production/reception of speech, virtual reality immersive programs (visual and/or auditory) and simple programs that require the user to vocalize from a prescribed set of written or audio materials.

Other training can relate to bridging the identified errors in the speech production and/or reception (e.g., the absence of high frequency information). The system could then automatically prescribe materials specific to improving the perception/reception of these materials (for example, provide materials specific to improving the 'sh' sound).

The system can provide inputs and/or advice on early language development in children with cochlear implants or other types of hearing prostheses whereby the system tracks the recipients vocal production against the expected trajectory after implantation and either contacts the educator or speech therapist/pathologist on the results or provides a customized speech therapy program for the carer or parent.

It is noted that the above exemplary adjustments to the hearing rehabilitation or habilitation regimes are but exemplary, and other adjustments can be utilized in the exemplary embodiments of method 1200. It is also noted that the above exemplary counseling scenarios are also exemplary, and other counseling scenarios can be utilized in the exemplary embodiments of method 1100.

Figure 13:
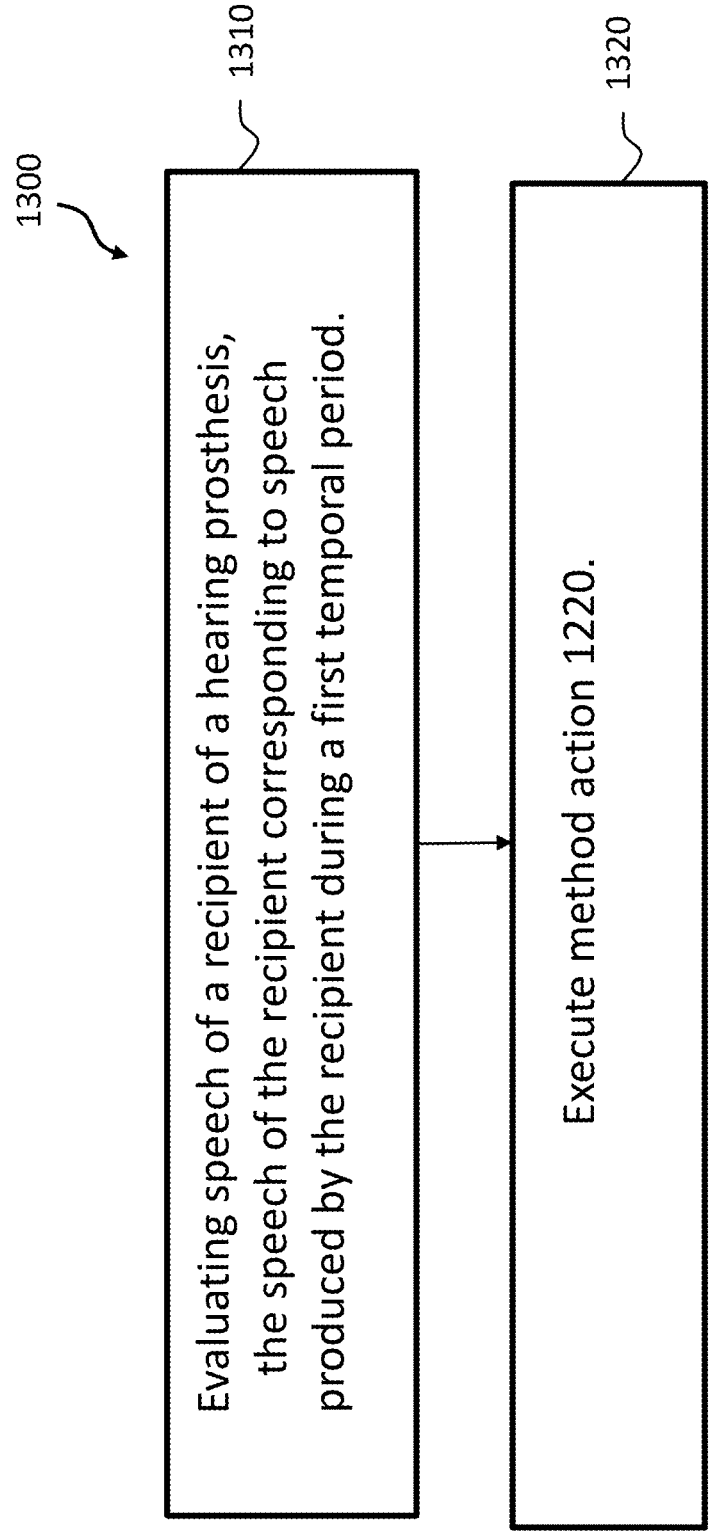
FIG. 13 depicts another exemplary flowchart for another exemplary method according to another exemplary embodiment.

FIG. 13 presents an exemplary flowchart for an exemplary method, method 1300, that also relates to the adjustment of a hearing habilitation and/or rehabilitation regime. Method 1300 includes method action 1310, which includes evaluating speech of a recipient of a hearing prosthesis, the speech of the recipient corresponding to speech produced by the recipient during a first temporal period. This can be done according to the any of the teachings detailed herein and/or variations thereof. In an exemplary embodiment, method action 1310 is executed by a hearing prosthesis, while in other embodiments, the method action 1310 is executed by a smart phone or by a remote device and/or by a remote audiologist, etc. Any device, system, and/or method of executing method action 1310 can be utilized in at least some exemplary embodiments. Method 1300 further includes method action 1320, which includes executing method action 1220 detailed above, which includes adjusting a hearing habilitation and/or rehabilitation regime of the recipient based on the evaluation, and thus the action of adjusting the hearing habilitation and/or rehabilitation regime can correspond to any of the exemplary embodiments detailed above and/or below in this regard.

In an exemplary embodiment, method action 1310 includes comparing the speech of the recipient to speech of the recipient produced during a second temporal period prior to the first temporal period. In this regard, method action 1310 has some similarities to the method 1000 presented above. In an exemplary embodiment, the comparison of the speech of the recipient in the two temporal periods can include identifying substitution errors related to voicing.

In an exemplary embodiment, the second temporal period of method action 1310 is a period prior to an implantation of the hearing prosthesis into the recipient. In an exemplary embodiment, the second temporal period of method action 1310 is a period prior to a fitting of the hearing prosthesis to the recipient. In an exemplary embodiment, the second temporal period of method action 1310 is a period prior to the acquisition of the hearing prosthesis by the recipient.

In an exemplary embodiment of method 1300, the action of evaluating the speech of the recipient includes acoustically analyzing patterns in the speech production of the recipient. In an exemplary embodiment, this can include identifying place and/or manner of articulation.

In an exemplary embodiment, the action of evaluating the speech of the recipient of method 1310 includes detecting problems with speech articulation (production) and/or phonological processes (sound patterns) and/or detecting difficulties with pronouncing sounds having relatively higher frequency components than that of other pronounced sounds. In an exemplary embodiment, the action of evaluating the speech of the recipient of method 1310 includes detecting slurred phoneme production and/or detecting difficulties with pronouncing sounds having relatively higher frequency components than that of other pronounced sounds.

In an exemplary embodiment of method 1300, the action of evaluating the speech of the recipient includes determining that the recipient is having problems hearing in a first set of sound conditions relative to that which is the case in a second set of sound conditions. In an exemplary embodiment, this can include determining that, for example, the recipient is having problems when exposed to speech of others when the recipient and the others are located inside a building vs. when exposed to speech of others when the recipient and the others are located indoors. This can have utilitarian value with respect to developing a counseling regime for the recipient. By way of example only and not by way of limitation, the recipient can be counseled to pay closer attention to people's lips when the recipient is located in a building. By way of example only and not by way of limitation, in an exemplary embodiment of method action 1320, the adjustment of the hearing habilitation and/or rehabilitation regime of the recipient can include instructing the recipient to spend more time outdoors.

It is to be understood that at least some of the teachings detailed herein enable the ability to determine that the recipient is having problems hearing in a first set of sound conditions relative to that which is the case in a second set of sound conditions.

Figure 14:
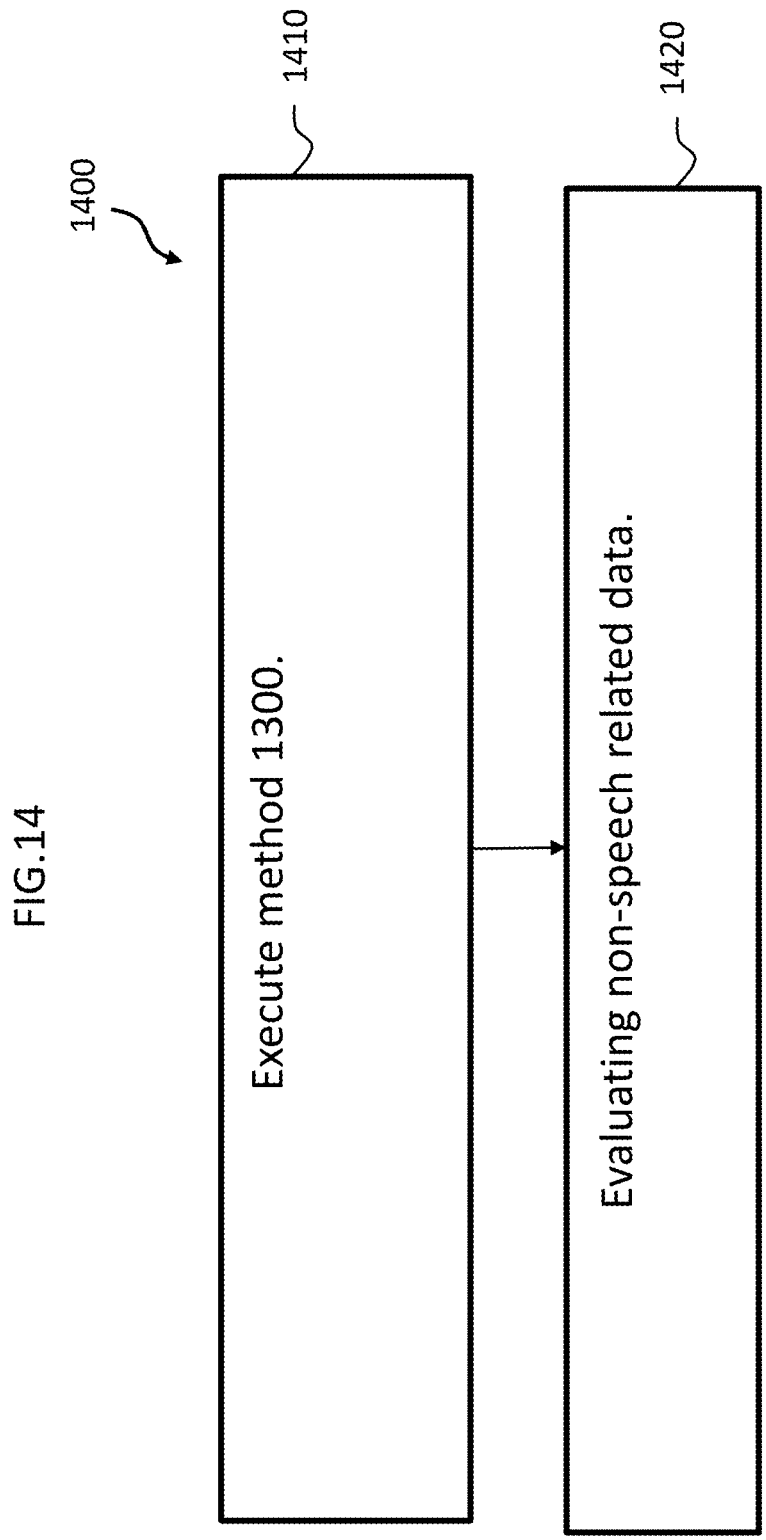
FIG. 14 depicts another exemplary flowchart for another exemplary method according to another exemplary embodiment.

FIG. 14 presents an exemplary method, method 1400, that includes method action 1410, which includes executing method 1300. Method 1400 further includes method action 1420, which includes evaluating non-speech related data. In an exemplary embodiment, non-speech related data can include, by way of example only and not by way of limitation, recipient age, recipient sex, recipient occupation, length of time of hearing impairment, length of time since acquisition/beginning of use of hearing prosthesis, age of onset of hearing impairment, native language of recipient, etc. In an exemplary embodiment, the action of adjusting the hearing habilitation and/or rehabilitation regime executed in method action 1320 is based on the evaluation of the non-speech related data. By way of example only and not by way of limitation, the hearing rehabilitation regime will be different for a recipient who has recently lost his or her hearing (e.g., within the past 4 months) versus one who has lost his or her hearing years prior. For example, with respect to the former, the rehabilitation regime can include exposure to more complex sounds/more complex speech relative to the latter.

Some exemplary embodiments rely on statistical models and/or statistical data in the variation evaluations detailed herein and/or variations thereof. The "nearest neighbor" approach will be described in greater detail below. However, for the moment, this feature will be described more broadly. In this regard, by way of example only and not by way of limitation, in an exemplary embodiment, the evaluation of speech of the recipient of method 1310 includes comparing the speech of the recipient to data of speech for similarly situated people who do not have hearing impairments. By way of example only and not by way of limitation, the biomarkers of the speech of a person who works as a bank teller who has a hearing impairment can be compared to the pertinent biomarkers of the speech a statistically significant group of people who also work as bank tellers. In an exemplary embodiment, the statistically significant group can include, for example, ten or more hearing people who speak the same language as the recipient and who are within 10 years of the age of the recipient (providing that the recipient is older than, for example, 30 years old, in some instances by way of example only and not by way of limitation), the same sex as the recipient, etc.

In an exemplary embodiment, a machine learning system, such as a neural network, can be used to analyze the speech data of the statistically significant group so as to enable (or better enable) the comparison. That said, in some exemplary alternate embodiments, the comparison of speech of the recipient can be performed against a statistically significant data pool a speech of other hearing impaired persons. Also, by way of example only and not by way of limitation, in an exemplary embodiment, the evaluation of speech of the recipient of method 1310 can include comparing the speech of the recipient to data of a speech development trajectory for similarly situated recipients. For example, if the recipient is a person who has received a cochlear implant three years ago, who had perfect hearing prior thereto, and who is 25 years old, the biomarkers of speech can be compared to biomarkers of a statistically significant group (e.g., a group of 10 people who are older than 20 years old but less than 40 years old who had a cochlear implant implanted 3 years prior to the acquisition of the data utilized to develop the statistically significant model and who had perfect hearing prior thereto, etc., again simply by way of example only and not by way of limitation). If the cochlear implant was implanted one year prior, the statistically significant group could be those who had cochlear implants implanted about one year prior to the acquisition of the data utilized to develop the statistically significant model. The idea with this feature of method 1300 is that the recipient speech can be utilized to gauge whether the recipient is progressing above average or below average relative to the statistically significant group. Thus, utilizing the recipient speech, or more accurately, utilizing the biomarkers of the recipient speech, and comparing such to a statistically significant model, the progress of the habilitation and/or the rehabilitation of the recipient can be better gauged in that there is a statistically significant population to which the recipient speech can be compared. This as opposed to simply comparing recipient speech to that which was the case prior to the comparison, were comparing the recipients speech to the speech of a normal hearing person, which would not have as much utilitarian value as the innovative approach described above, at least in some instances.

It is noted that at least some exemplary embodiments also utilize the speech of others to gauge or otherwise evaluate the recipients hearing, and such actions can be combined with the utilization of a statistically significant population. In this regard, in an exemplary embodiment, the methods with respect to capturing sound include capturing sound that corresponds to the speech of others during a first temporal period. The actions of evaluating the captured sound detailed herein can include comparing the complexity of the captured speech to a statistical model of speech exposure and determining, based on the comparison, that the recipient is exposing himself or herself to less complex speech due to the ability of the recipient to hear. For example, human beings will often consciously or subconsciously avoid difficult situations. There are instances where human beings will avoid situations where he or she is having difficulty, or at least having relative difficulty hearing. Thus, in at least some scenarios, a person who is hard of hearing can find himself or herself avoiding certain types of sounds, or, more accurately, will avoid exposing himself or herself to situations where the sound environment presents difficulties for him or her. This can be the case with respect to conversation environments. That is, the recipient may begin to avoid, consciously or subconsciously, environments where it is difficult to hear or otherwise understand what people are saying to him or her. Thus, in an exemplary embodiment, by evaluating the speech of others directed towards the recipient (directly, as in the case of a conversation, or indirectly, as is the case may be with respect to a political speech or a lecture or seminar, or the type of television or radio he or she listens to), which speech can be captured according to the teachings detailed herein and/or variations thereof, the speech can be evaluated to gauge the recipients ability to hear. Based on various factors with respect to a statistically significant group, the complexity of the captured speech of others can be compared to a statistical model of typical speech exposure of a statistically significant group, and if it is found that the recipient is subjecting himself or herself to less complex speech relative to the statistically significant model, a determination can be made the recipient is having difficulty hearing. Still further, the types of speech that the recipient is exposed to can also be utilized, in some instances, to evaluate more specific types of hearing loss of the recipient (e.g., if the speaker is avoiding people who are native French language speakers, or avoiding speaking with women, a determination can be made that the recipient is having difficulties with higher frequency speech).

In an exemplary scenario, there is a recipient who is politically active in his or her mid-60s who is retired and widowed, who has distinct political tendencies. The statistical model that could be relevant to this person is a retired person who listens to talk radio for at least 4 hours per day and watches news programming in the evening for at least 2 hours, or at least at a higher level relative to non-politically inclined persons. If the captured sound indicates that the person is listening to less talk radio (e.g., listens for a half hour or so, but then turns the radio off, or to something else) and is not watching certain news programming (or limits himself or herself to the amount of the certain news programming) that at least the average member of the statistically significant population group listens to, a determination can be made that the person is having difficult time listening to complicated speech and/or fast talking people and/or people talking at the same time. Alternatively, in an exemplary embodiment, if the recipient is of a demographic that is inclined to watch "sitcoms," but the recipient watches less relative to a statistically significant group, a determination to be made that the "laugh track" could be causing difficulty for the recipient.

Note that much of the above has focused on the "demographic" of the recipient to identify the relative statistically significant population. Alternatively and/or in addition to this, the recipient could be queried as to his or her desires. For example, the recipient could state that he or she likes to listen to talk radio or likes to watch sitcoms. Thus, based on this data, the statistically significant population could be identified.

Note that the statistically significant population could be a population of people who are also hard of hearing, or could also be a population of people who are not hard of hearing. That is, in an exemplary embodiment, the demographics of the person could be correlated to that of a normal hearing person to extrapolate the fact that the recipient is having a hard time hearing certain types of sounds.

In view of the above, it is to be understood that in at least some exemplary embodiments, there is a body worn or implantable hearing prosthesis, such as that represented by the prosthesis of FIG. 2, wherein, when the hearing prosthesis is functioning according to the algorithm of FIG. 4 (algorithm 400), the identified one or more biomarkers are linguistic characteristics of people other than the recipient, and the hearing prosthesis is configured to identify the linguistic characteristics as such. This can have utilitarian value with respect to the ability of comparing the speech of others to the above noted statistically significant models, amongst other utilities. Also, in an exemplary embodiment, by identifying the speech of others, or at least identifying the biomarkers as biomarkers of the speech of others, the amount of data stored by the hearing prosthesis and/or the amount of data transmitted by the hearing prosthesis to the remote component (e.g. smart phone, remote computer, etc.) can be limited relative to that which will be the case if all sounds and/or all speech sounds were stored and/or transmitted.

While the embodiments detailed above have been described in terms of comparing the speech of others to a statistically significant group/a model of a statistically significant population, in some other embodiments, the evaluation of the speech of others can be executed without the utilization of statistical models. In this regard, with reference to the algorithm of FIG. 4, by way of example only and not by way of limitation, the one or more biomarkers of method action 430 include one or more first biomarkers of people other than the recipient and the hearing prosthesis is configured to identify the first biomarkers as such. Further, with continued reference to the algorithm of FIG. 4, the one or more biomarkers also include second biomarkers of the recipient, and the hearing prosthesis is configured to identify the second one or more biomarkers as such. In this exemplary embodiment, instead of comparing the first biomarkers to a statistically significant group and/or instead of comparing the second one or more biomarkers to a statistically significant group, the hearing prosthesis is configured to compare the one or more first biomarkers to the one or more second biomarkers and develop data indicative of the recipients ability to hear (although in some embodiments, the various biomarkers can also be compared to a statistically significant group as well). In this exemplary embodiment, by comparing the various biomarkers, a determination can be made as to how well the recipient's hearing. For example, in a scenario where the recipient is engaging in a conversation where certain words are utilized that are relatively rarely used in conversation in general, but reoccur in this conversation (e.g., "heat treated," "cattle futures," "Skywalker," etc.), a comparison can be made as to the sound of those words spoken by the people other than the recipient and the sound of those words spoken by the recipient. If the sound is different, at least within certain predetermined tolerances, a determination can be made that the recipient is having difficulty hearing certain sounds because the recipient would be able to pronounce those sounds "better" or "more accurately" if he or she could hear the sounds. Such can be the case because the recipient would have just recently heard those sounds coming from the person other than the recipient, and thus the recipient should be expected to at least "mimic" those sounds in his or her speech. The inability to mimic those sounds can be indicative of an inability to hear those sounds properly.

Figure 15:
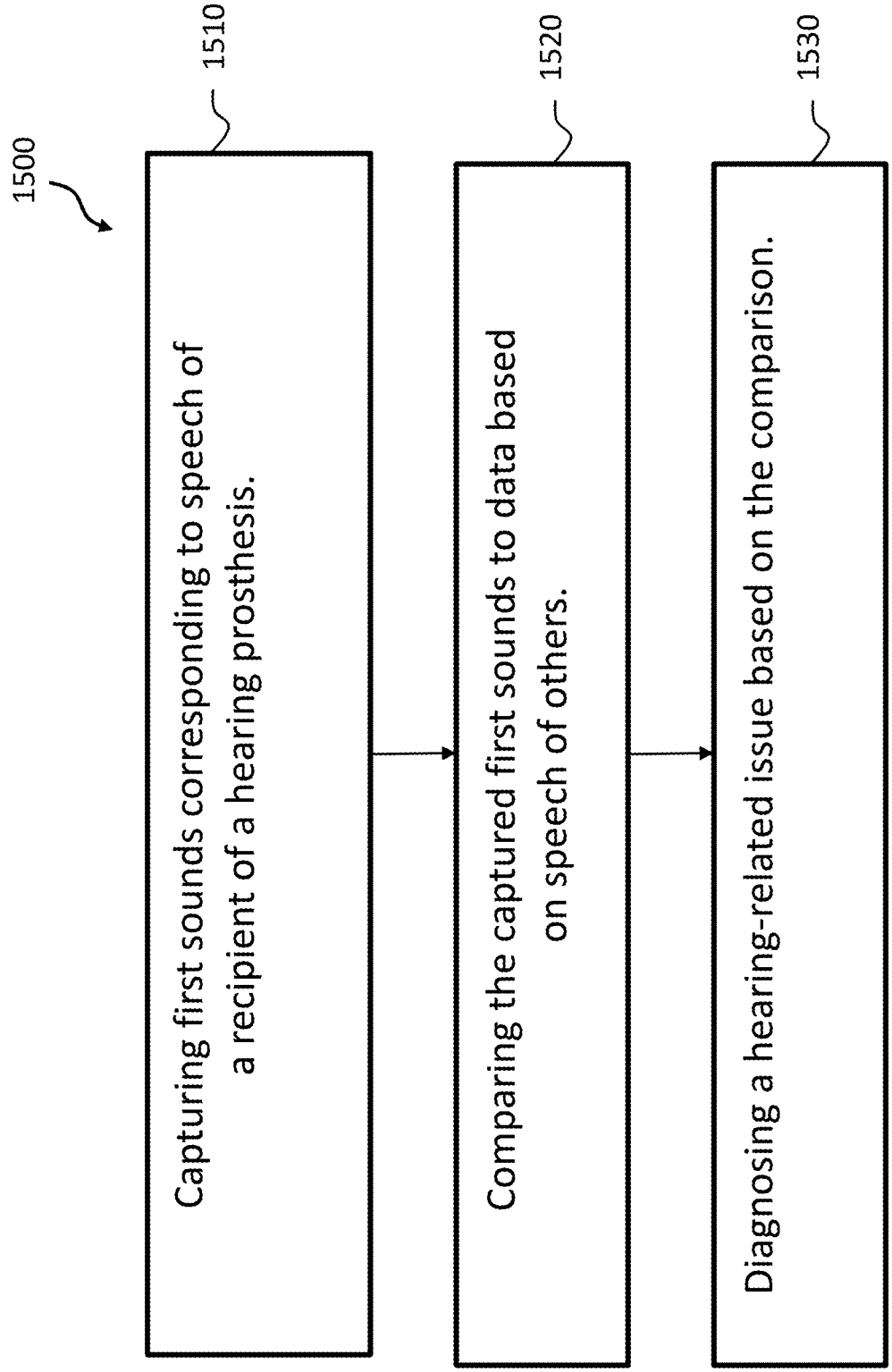
FIG. 15 depicts another exemplary flowchart for another exemplary method according to another exemplary embodiment.

FIG. 15 represents an exemplary method, method 1500, based in part upon the utilization of speech of others. More specifically, method 1500 includes method action 1510, which includes capturing first sounds corresponding to speech of a recipient of a hearing prosthesis. Note that method action 1510 can be executed by the hearing prosthesis, or can be executed by another device, such as by way of example only and not by way of limitation, the microphone of a smart phone (or a regular phone), the microphone of a computer, with the microphone of a traditional recorder. Any device, system, and/or method that can enable the execution of method 1510 can be utilized in at least some exemplary embodiments. Method 1500 further includes method action 1520, which includes the action of comparing the captured first sounds captured in method action 1502 data based on the speech of others. Again, in an exemplary embodiment, the data based on speech of others can correspond to the model of the statistically significant group detailed above. In an exemplary embodiment, the data based on speech of others can correspond to the first biomarkers detailed in the paragraph immediately above this paragraph. Method 1500 further includes method action 1530, which includes diagnosing a hearing-related issue based on the comparison. Method action 1530 includes both the comparison to people whom the recipient interacts and a comparison to the statistically significant population. Thus, in an exemplary embodiment, the method of 1500 further includes the action of capturing second sounds corresponding to one or more voices of others, wherein the data based on the speech of others is based on the second sounds that are capture. Further, in an exemplary embodiment, the data based on speech of others is statistical data of a statistical relevant population. Is noted that the two are not mutually exclusive.

By "hearing-related issue," it is meant any feature indicative of the recipients ability to hear, whether that be frequency based or otherwise. For example, in cochlear implant recipients. the spoken pronunciation can be skewed by the recipient hearing pronunciation differently to what a normal hearer might hear. This skewing of pronunciation, for example, could be due to a level imbalance of low and high frequencies. Because the recipient is hearing high frequencies at a lower level than the low frequencies they may have a lower level when they produce high frequencies. Other speech production problems might be with the features of speech, such as, for example, intonation, stress, length, and or fundamental frequency characteristics.

In some instances, there are systemic differences between the child and adult speech production. In some instances, the children and adults with hearing impairment have both variable speech production, diverging significantly from their normal hearing peers. The divergence from normal hearing production can be generally described as substitution errors relating to voicing, place and manner of articulation and/or segment omissions. Finer grain analysis of the speech production differences is possible that investigates the aspects of the production such as voicing contrasts, consonant substitution and omission, frequency characteristics, voice quality, intonation patterns, speaking rate, formant transitions etc.

In some embodiments, any of the above phenomenon of the preceding two paragraphs can be considered "hearing-related issues."

In an exemplary embodiment, the action of diagnosing the hearing related issue of method action 1530 includes determining that the recipient should increase exposure time to more-complex second sounds relative to that which was previously the case. In this regard, in at least some exemplary scenarios, the recipient's ability to hear, or, more accurately, the recipient's ability to understand and pronounce words, can be improved by increasing the exposure to complex sounds. For example, increasing the amount of time listening to on-line lectures or audio books can have utilitarian value as compared to listening to music, etc.

It is noted that in an exemplary embodiment, the method of FIG. 15 is executed where the recipient is a pre-adolescent recipient. In an exemplary embodiment, the recipient is 2, 3, 4, 5, 6, 7, 8, 9, 10, 11, 12, 13, 14, 15, 16, 17, 18, 19, 20, 21, 22, 23, 24, 25, 26, 27, 28, 29, 30 years old or more, or any value or range of values therebetween in 0.1 year increments (e.g., 2.3 years old to 3.1 years old, 22.2 years old, etc.). In an exemplary embodiment, the recipient is at or between 20 and 30 years old, at or between 25 and 35 years old, at or between 30 and 40 years old, at or between 35 and 45 years old, at or between 50 and 60 years old, at or between 55 and 65 years old, at or between 60 and 70 years, old, or older than 70 years old.

In some embodiments, a pre-adolescent's language production can be tracked (e.g., captured with a smart device or remote microphone or the microphone of the hearing prosthesis) and stored in a table of frequently used words that are cross-checked by the parent or caregiver at the clinical session or remotely via a web interface. Changes either by way of improvement or decrement can be employed to guide the clinical management of the child and possibly recommend rehabilitation and education programs. In at least some exemplary embodiments, the teachings detailed herein and/or variations thereof are utilized to automatically acquire and automatically store the produced speech and/or biomarkers. This as opposed to having to be manually recorded by a parent or caregiver.

In an exemplary embodiment of the method of FIG. 15, the hearing prosthesis is a cochlear implant, and the hearing related issue is a sub-performance map setting of the cochlear implant. In this regard, in an exemplary embodiment, based on the recipient speech, a determination can be made that the map setting of the cochlear implant should be adjusted. By way of example only and not by way of limitation, if the analysis determines that the recipient is having a difficult time perceiving high-frequency sounds based on the comparison in method action 1520 (e.g., the recipient is having difficulty pronouncing the "sh" consonant, or is omitting such from words, etc.), a determination can be made that the map setting of the cochlear implant is not as good as it otherwise could be. Thus, remapping the cochlear implant could have utilitarian value with respect to helping a recipient to hear better. Indeed, in an exemplary embodiment, this remapping can occur automatically or semi-automatically. In an exemplary embodiment, real-time map adjustments, based on the biomarkers, can be executed. In an exemplary embodiment, an intelligent algorithm can be utilized to evaluate the biomarkers and adjust the mapping parameters and/or assess the change of the biomarkers. In an exemplary embodiment, this can be an iterative process in that the biomarkers can be evaluated to determine how the adjustments to the map have impacted the recipient's speech, and thus by proxy, the recipients hearing, and then intelligent algorithm can make subsequent adjustments to the map.

The teachings detailed herein and variations thereof can utilize a broad system, and can be implemented in combination with other factors for wide effect.

As noted above, in an exemplary embodiment, data from the statistically significant population is utilized to develop statistical models to which the speech of the recipient is compared. In an exemplary embodiment, speech and/or biomarkers from a statistically significant population of speakers is captured in accordance with the teachings detailed herein and/or variations thereof and pooled into a central location (e.g., uploaded to the cloud) and stored. The stored data is used to provide the ability to characterize features of the speech for a given population. In an exemplary embodiment, the pulling is utilized to develop the statistically significant models in general, and to develop the "nearest neighbor" information in particular. In at least some exemplary embodiments, the data analysis is segmented based on attributes, such as device type or sub-type, age, duration of hearing loss, genetics, etc. The data mining exercise can extend the input to the clinical map parameters in an effort to look for trends across mapping parameters. Thus, over time, statistically significant models can be developed. Analysis of the recipient's biomarkers can be done be assigning a classification group where recipients have been grouped based on biomarkers and outcomes. In some exemplary embodiments, groups with similar biomarkers will have similar hearing prosthesis outcomes. This data can be utilized to predict outcomes. This data can also be used for initial fitting of a device as certain groups might have a quicker and/or better outcome with a particular fitting. Such on-going classification and analysis evolves the underlying management model, thereby improving the model and the suggested clinical practices.

Thus, in some embodiments, a recipient-centric approach can utilize a regime where biomarkers are anchored against a so-called "nearest neighbor" type approach (e.g., people like the recipient, statistically speaking (demographically, length of time of hearing loss (including never having had normal hearing), occupation, type and model of hearing prosthesis, speech processing algorithm utilized by the hearing prosthesis, etc.) would be expected to have certain speech biomarkers at the time that commencement of utilization of the hearing prosthesis occurs, and would have certain speech biomarkers 3 months out, and certain speech biomarkers 6 months out, 1 year out, 18 months out, 2 years out, 3 years out, 4 years out, 5 years out, 6 years out, etc.). Any of the disclosed utilization of biomarkers detailed herein can utilize this approach.

In an exemplary embodiment, data is pulled from various recipients of hearing prostheses to create statistically significant models. As part of a treatment regime, an audiologist selects a pertinent statistical model (or such is selected using a machine algorithm—any method of selecting the pertinent model can be utilized in at least some exemplary embodiments) and the biomarkers that are collected are compared to this statistically significant model to evaluate the progress/status of the hearing prosthesis.

Figure 16:
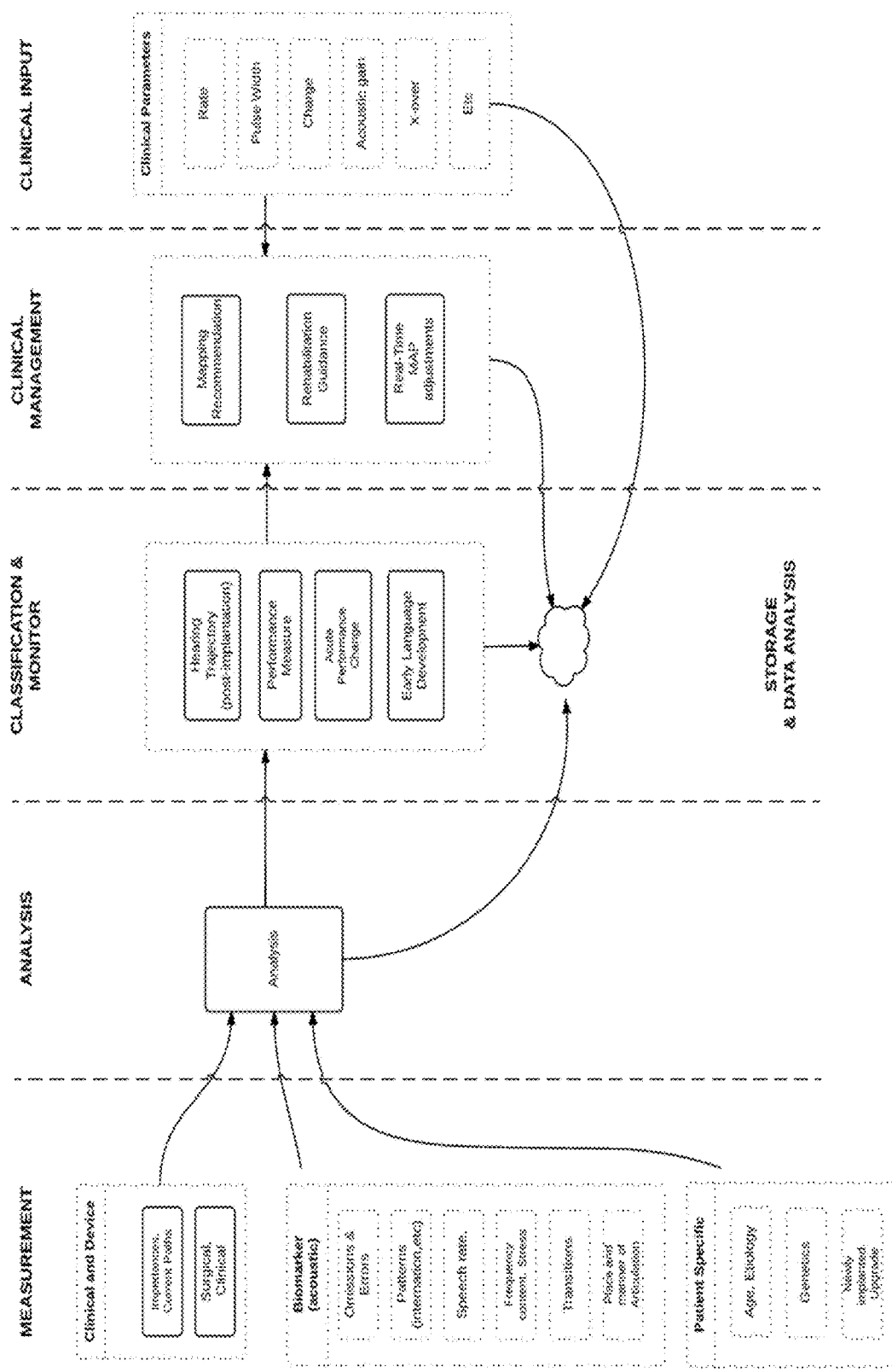
FIG. 16 depicts an exemplary functional schematic conceptually representing a system according to an exemplary embodiment.

FIG. 16 presents a schematic functionally representing some of the features usable in some of the exemplary embodiments detailed herein, and functionally represents a general flow of an exemplary method where acoustic biomarkers from the recipient's produced speech (or other speech in some alternate embodiments) are analyzed in conjunction with the clinical device and/or patient specific information, as pre-processing prior to the classification, where the classification derives recipient specific recommendations or guidance (clinical management) for one or more of an intelligent system, the hearing professional, or the recipient. In this exemplary embodiment, the biomarkers can be collected and analyzed using two methods. First, dedicated speech testing can be utilized, which can include sitting in front of a personal computer or tablet or the like, or can include speaking into a telephone. Such can be executed in so called "point of care" sessions in the clinical setting and/or in so-called "remote care" settings, at home or remote from a central care provider. Alternatively, or in addition to this, real-time monitoring and/or real-time analysis of the speech for biomarkers can be implemented, such as, by way of example only and not by way of limitation, by utilizing a so-called "own voice detector" to provide a determination that the recipient has begun speaking.

With reference to FIG. 16, the measurement (e.g., sound capture) can occur at the clinic and/or remotely, using the hearing prosthesis or other devices, where one or more biomarkers can be utilized in the measurements, such as by way of example only and not by way of limitation, omission and/or errors, patterns, speech rate, frequency content, stresses, transitions, and/or place and/or manner of articulation. Additional data can be collected at the measurement stage, such as by way of example only and not by way of limitation, patient specific information such as age, etiology, genetic information, and information about the hearing prosthesis, such as by way of example, the length of time from when a cochlear implant was implanted, whether or not the hearing prosthesis has been upgraded etc. Some or all of this information is utilized at the analysis stage so as to classify and/or monitor certain facets related to hearing. By way of example only and not by way of limitation, the post implantation and/or post receipt hearing trajectory can be monitored, performance measurements can be made, acute performance changes can be identified, and/or early language development can be evaluated.

The results of this classification and monitoring can be stored in the cloud in at least some exemplary embodiments, as represented in graphical terms in FIG. 16. The data from the classification and monitoring stage can be utilized for clinical management of the recipient more specifically, at the clinical management stage, a mapping recommendation and/or a remapping recommendation can be developed, rehabilitation and/or habilitation guidance can be provided, and real-time map adjustments can be made based on the data obtained by the classification of monitoring stage. As is graphically illustrated, the results of the clinical management stage can be uploaded to the cloud, which can be in turn utilized to adjust a feature of the hearing prosthesis and/or adjust a habilitation and/or rehabilitation regime, and/or otherwise utilized to counsel the recipient to take certain actions and/or avoid certain actions. As seen in FIG. 16, clinical input can be provided with respect to adjustments to the hearing prostheses, such as by way of example only and not by way of limitation, the adjustment of a crossover point for a multimodal hearing prosthesis, the adjustment of acoustic gain (frequency global or frequency local, etc.), pulse with modifications, stimulation rate modifications, etc. Clinical input can entail any adjustments or arrangements that can provide utilitarian value. Note that the clinical input can be provided based on the evaluation of a trained audiologist or the like, and/or can be provided in an automated manner. Any arrangement of implementing the teachings detailed herein can be utilized in at least some exemplary embodiments.

Figure 17:
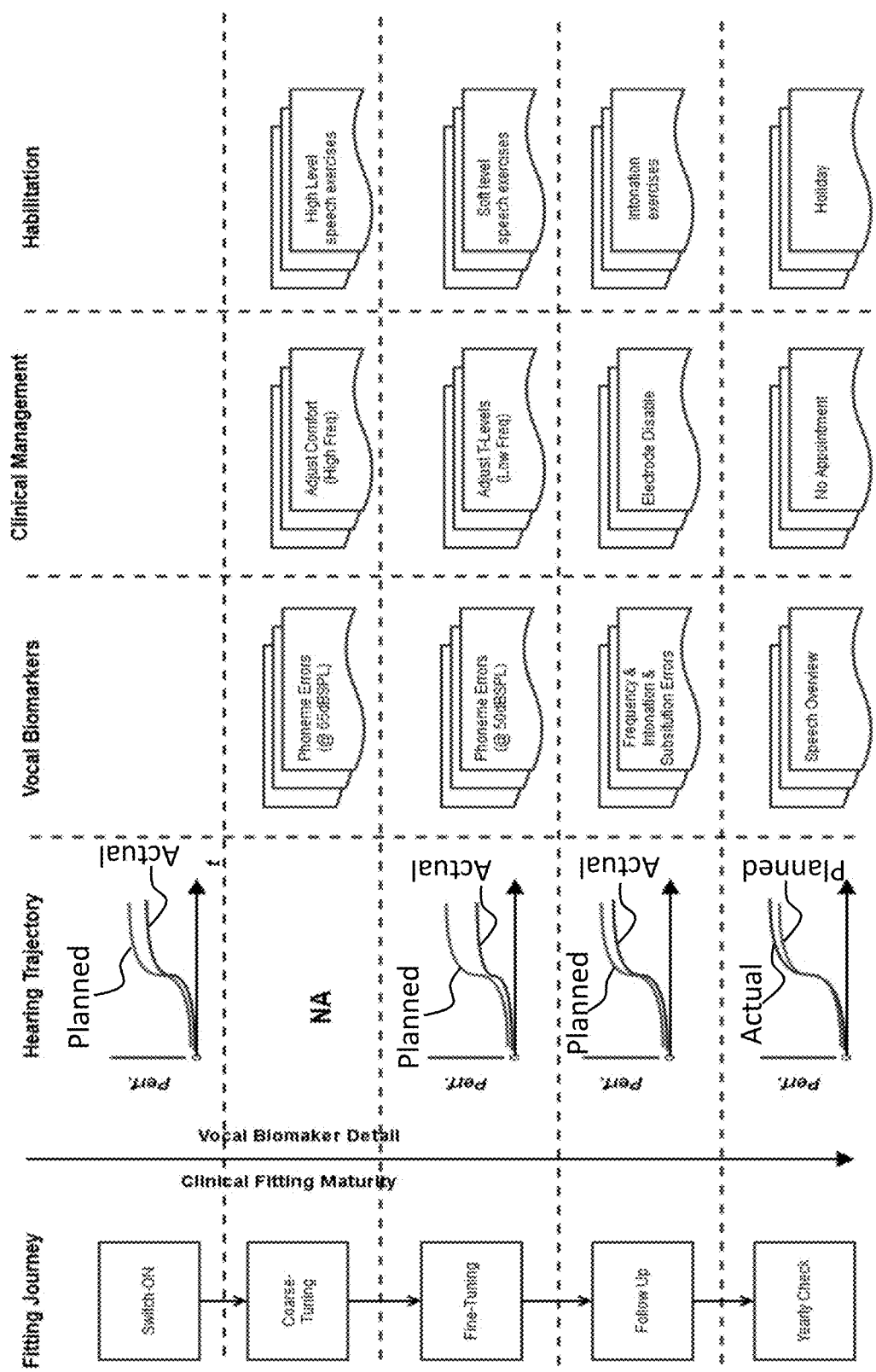
FIG. 17 depicts an exemplary schematic representing time based tiers applicable to some of the teachings detailed herein.

FIG. 17 presents a quasi-functional schematic representing a clinical example utilizing at least some of the teachings detailed herein with respect to a cochlear implant. The schematic is divided into columns where location along the column represents time progress. The hearing trajectory is seen in graphical format with performance versus time. Various vocal biomarkers are listed, coupled with the clinical management and habilitation (or rehabilitation) action taken. With respect to the graphs depicting the planned versus actual performance of the recipient, in at least some exemplary embodiments, the performance constitutes a characterization of the recipients hearing performance compared to time, where the planned curve can be compared to the actual curve to determine how well the recipient is performing with the prosthesis in the real world, relative to the expected trajectory (which can be developed based on a statistically significant population, as noted above). The healthcare professional can evaluate the hearing trajectory curves and determine whether or not an intervention is utilitarian. That said, alternatively and/or in addition to this, the hearing trajectory curves can be evaluated in an automated or semi-automated fashion, and a determination whether or not an intervention is utilitarian can be made automatically, which intervention can be executed automatically or semi-automatically. Note that the hearing trajectory curves can be utilized to diagnose or otherwise identify acute performance changes. Indeed, such can have utilitarian value with respect to identifying difficulty with hearing in an automated fashion, where such difficulty, when identified, can be automatically indicated an elevated to a health care professional for evaluation.

Note also that the hearing trajectory curves can have utilitarian value with respect to monitoring the early language development of a child and/or a pre-adolescent. In this regard, the recipient's speech can be evaluated and determinations can be made as to how well the recipient is hearing with his or her hearing prosthesis, and adjustments can be made to the hearing prosthesis and/or to the habilitation and/or rehabilitation regime.

An exemplary embodiment of a method of real time or staggered time monitoring with respect to a system for implementing the teachings herein and/or variations thereof will now be described.

In an exemplary embodiment, a recipient of a hearing prosthesis, such as a cochlear implant implantee, speaks in a manner such that sound is captured by the sound capture device of the cochlear implant. In an exemplary embodiment, the sound capture device is a microphone located on a behind the ear device, which behind the ear device includes a speech processor. In an exemplary embodiment, the behind the ear device includes an own voice determination algorithm that enables the prosthesis to identify when the recipient is speaking. Utilizing the own voice determination algorithm, the behind the ear device samples the recipient speech to obtain biomarkers thereof. Based on this own voice determination selected speech, the captured speech and/or the biomarkers of the captured speech (where, for example, the behind the ear device can include software and/or firmware to extract the pertinent biomarkers from the captured speech) is streamed to a remote component, such as a smart phone or a tablet or a computer or the like. The smart phone or other remote component can analyze the data stream thereto to extract biomarkers and/or can act as a medium to pass the data stream thereto to the cloud for cloud computing. That is, the smart phone or other remote device passes the collected information from the remote device to the cloud.

The system includes a link from the cloud to a clinic to pass the information uploaded to the cloud to the clinic, where the information can be analyzed. At the clinic, the information is analyzed and changes to the habilitation and/or rehabilitation regime are developed and/or changes to the settings of the hearing prosthesis are developed. These changes are then uploaded to the cloud, and then down linked from the cloud to the smart device to inform the recipient of the hearing prosthesis of the decisions/appointments/training that is relevant to him or her and/or to inform the recipient of changes that are utilitarian to the hearing prosthesis that he or she should implement. In an alternative embodiment, the smart device controls the settings of the hearing prosthesis and automatically adjusts the settings of the hearing prosthesis.

Another exemplary system includes a smart device, such as a smart phone or tablet, etc., that includes a sound capture device, that is running a purpose built application that detects those vocal acoustic biomarkers. In this exemplary system, the hearing prosthesis is bypassed or otherwise not utilized. Indeed, in this exemplary system, a hearing prosthesis is not be utilized at all. That is, in an exemplary embodiment, the person that is speaking is not a recipient of the hearing prosthesis, but instead a subject who could be hard of hearing. The smart device detects vocal acoustic biomarkers. In an exemplary embodiment, the smart device can be configured to present a series of words for the recipient to repeat, which words are words that have been preselected for the purpose of identifying hearing attributes based on the speech of hearer/subject. In this regard, the hearer/subject vocalizes the visual signals that are presented on the smart device (e.g., speaks the words displayed on the smart device). The subject speech is then picked up by the smart device's microphone. The smart device either uploads the speech to the cloud or otherwise analyzes the speech to identifying the biomarkers and uploads the biomarkers to the cloud. Alternatively, the smart device can analyze the speech autonomously according to the teachings detailed herein. In an exemplary embodiment, the cloud stores the results of the tests across all subjects, and data can be sent to the relevant clinic, where the data can be analyzed, and recommendations for changes can be provided back to the cloud to the recipient via the smart device.

In view of the above, at least some embodiments provide an objective and evidence-based measure of clinical performance of a hearing prosthesis user, such as by way of example only and not by way of limitation, a cochlear implantee. The prosthesis of FIG. 2, or variations thereof, provide the ability to execute a method that includes the acoustic analysis of the recipient's own voice to derived a number of metrics, such as acoustic biomarkers. The method can be employed by intelligent systems to provide feedback to the implantee and/or heath care professionals to assist with the clinical management of the recipient.

It is briefly noted that in some embodiments, the user interface 280 and an external processor 282 can correspond to any of the systems detailed herein for accessing data of the hearing prosthesis related to speech, etc., or any other data detailed herein that enables the teachings detailed herein. Thus, 280/282 can be different than fitting systems, although in other embodiments, 280/282 can include the functionality of a fitting system. Although a cable 284 is shown in FIG. 1A between implant 200 and interface 280, a wireless RF communication may also be used along with remote 286.

Figure 18:
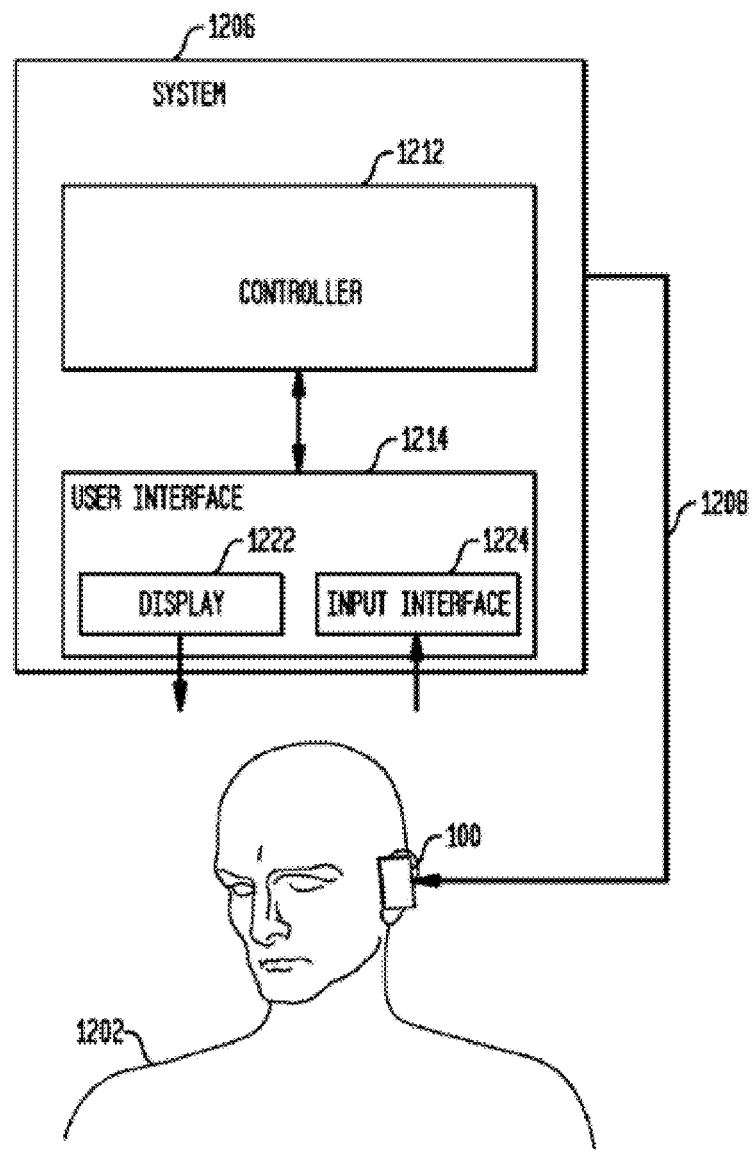
FIG. 18 depicts a schematic functionally representing an exemplary system.

FIG. 18 presents a functional schematic of a system with which some of the teachings detailed herein and/or variations thereof can be implemented. In this regard, FIG. 18 is a schematic diagram illustrating one exemplary arrangement in which a system 1206 can be used to execute one or more or all of the method actions detailed herein in conjunction with the use of a hearing prosthesis 100. System 1206 will be described, at least in part, in terms of interaction with a recipient. In an exemplary embodiment, system 1206 is a recipient controlled system. In an exemplary embodiment, system 1206 can correspond to a remote device and/or system, which, as detailed above, can be a portable handheld device (e.g., a smart device, such as a smart phone), and/or can be a personal computer, etc.

In an exemplary embodiment, system 1206 can be a system having any of the functionality according to the method actions detailed herein. In the embodiment illustrated in FIG. 18, a hearing prosthesis 100 can be connected to system 1206 to establish a data communication link 1208 between the hearing prosthesis 100 and system 1206. It is briefly noted that the following will be described in terms of element 100 corresponding to a hearing prostheses. However, it is noted that element 100 described in such terms is a proxy for any device that can enable the teachings detailed herein. By way of example only and not by way of limitation, element 100 can be a smart phone or a telephone or a computer or any device that could have captured the data upon which the methods detailed herein are utilized or otherwise contains data captured elsewhere. That is, while the following will be described in terms of a hearing prostheses. Any such disclosure below also corresponds to any other device that can enable the teachings detailed herein these are the obtaining the data and/or processing the data of the methods detailed herein.

System 1206 is bi-directionally coupled by a data communication link 1208 with hearing prosthesis 100 (or whatever device corresponds to element 100). Any communications link that will enable the teachings detailed herein that will communicably couple the implant and system can be utilized in at least some embodiments.

System 1206 can comprise a system controller 1212 as well as a user interface 1214. Controller 1212 can be any type of device capable of executing instructions such as, for example, a general or special purpose computer, a handheld computer (e.g., personal digital assistant (PDA)), digital electronic circuitry, integrated circuitry, specially designed ASICs (application specific integrated circuits), firmware, software, and/or combinations thereof. As will be detailed below, in an exemplary embodiment, controller 1212 is a processor. Controller 1212 can further comprise an interface for establishing the data communications link 1208 with the hearing prosthesis 100. In embodiments in which controller 1212 comprises a computer, this interface may be, for example, internal or external to the computer. For example, in an exemplary embodiment, controller 1206 and cochlear implant may each comprise a USB, Firewire, Bluetooth, Wi-Fi, or other communications interface through which data communications link 1208 may be established. Controller 1212 can further comprise a storage device for use in storing information. This storage device can be, for example, volatile or non-volatile storage, such as, for example, random access memory, solid state storage, magnetic storage, holographic storage, etc.

In an exemplary embodiment, controller 1212 is configured to execute any of the analytical and/or data storage and/or data manipulation teachings detailed herein and/or variations thereof.

User interface 1214 can comprise a display 1222 and an input interface 1224 (which, in the case of a touchscreen of the portable device, can be the same). Display 1222 can be, for example, any type of display device, such as, for example, those commonly used with computer systems. In an exemplary embodiment, element 1222 corresponds to a device configured to visually display a plurality of words to the recipient 1202 (which includes sentences), as detailed above.

Input interface 1224 can be any type of interface capable of receiving information from a recipient, such as, for example, a computer keyboard, mouse, voice-responsive software, touchscreen (e.g., integrated with display 1222), microphone (e.g. optionally coupled with voice recognition software or the like) retinal control, joystick, and any other data entry or data presentation formats now or later developed. It is noted that in an exemplary embodiment, display 1222 and input interface 1224 can be the same component, e.g., in the case of a touch screen). In an exemplary embodiment, input interface 1224 is a device configured to receive input from the recipient indicative of a choice of one or more of the plurality of words presented by display 1222.

It is noted that in at least some exemplary embodiments, the system 1206 is configured to execute one or more or all of the method actions detailed herein, where the various sub-components of the system 1206 are utilized in their traditional manner relative to the given method actions detailed herein.

In an exemplary embodiment, the system 1206, detailed above, can execute one or more or all of the actions detailed herein and/or variations thereof automatically, at least those that do not require the actions of a recipient.

An exemplary embodiment includes utilizing system 1206 to execute one or more or all of the methods detailed herein, or any one or more method actions of any method as applicable to the specific component of system 1206 In a similar vein, an exemplary embodiment is such that system 1206 is configured to execute any method detailed herein, or any one or more method actions of any method as applicable to the specific component of system 1206.

While the above embodiments have been described in terms of the portable handheld device obtaining the data, either directly from the recipient or from the hearing prosthesis, and performing a given analysis, as noted above, in at least some exemplary embodiments, the data can be obtained at a location remote from the recipient, and thus the hearing prosthesis 100. In such an exemplary embodiment, the system 1206 can thus also include the remote location (e.g., clinic).

In this vein, it is again noted that the schematic of FIG. 18 is functional. In some embodiments, a system 1206 is a self-contained device (e.g., a laptop computer, a smart phone, etc.) that is configured to execute one or more or all of the method actions detailed herein and/or variations thereof. In an alternative embodiment, system 1206 is a system having components located at various geographical locations. By way of example only and not by way of limitation, user interface 1214 can be located with the recipient (e.g., it can be the portable handheld device 240) and the system controller (e.g., processor) 1212 can be located remote from the recipient. By way of example only and not by way of limitation, the system controller 1212 can communicate with the user interface 1214, and thus the portable handheld device 240, via the Internet and/or via cellular communication technology or the like. Indeed, in at least some embodiments, the system controller 1212 can also communicate with the user interface 1214 via the Internet and/or via cellular communication or the like. Again, in an exemplary embodiment, the user interface 1214 can be a portable communications device, such as, by way of example only and not by way of limitation, a cell phone and/or a so-called smart phone. Indeed, user interface 1214 can be utilized as part of a laptop computer or the like. Any arrangement that can enable system 1206 to be practiced and/or that can enable a system that can enable the teachings detailed herein and/or variations thereof to be practiced can be utilized in at least some embodiments.

Figure 19:
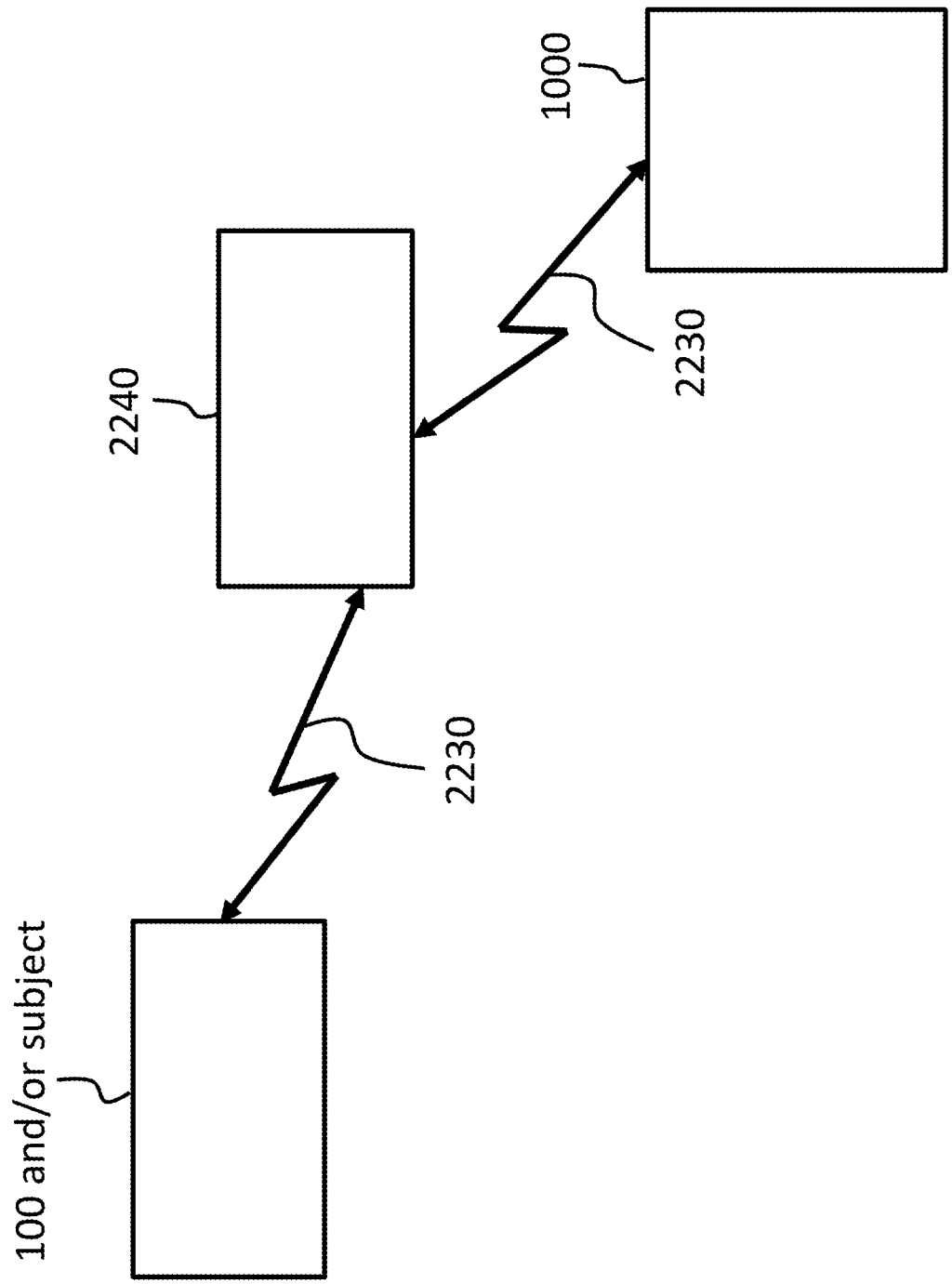
FIG. 19 depicts a schematic functionally representing another exemplary system.

In view of the above, FIG. 19 depicts an exemplary functional schematic, where the portable hand-held device 2240 is in communication with a geographically remote device/facility 1000 via link 2230, which can be an internet link. The geographically remote device/facility 1000 can encompass controller 1212, and the remote device 240 can encompass the user interface 1214. The geographic remote device/facility 1000 can be the clinic. It is also noted that in the embodiment of FIG. 18, link 2230 can represent communication between the portable handheld device 2240 and the hearing prosthesis 100 and/or can represent communication between the portable handheld device 2240 and the subject (bypassing the hearing prosthesis).

Accordingly, an exemplary embodiment entails executing some or all of the method actions detailed herein where the recipient of the hearing prosthesis or other subject, the hearing prosthesis 100 and/or the portable handheld device 2240 is located remotely (e.g., geographically distant) from where at least some of the method actions detailed herein are executed.

In an exemplary embodiment, the portable handheld device 2240 is configured to execute one or more or all of the method actions detailed herein. In an exemplary embodiment, the portable handheld device 2240 is configured to communicate with the cloud as detailed above and/or with the clinic as detailed above.

An exemplary embodiment includes utilizing system of FIG. 19 to execute one or more or all of the methods detailed herein, or any one or more method actions of any method as applicable to the specific component of the system of FIG. 19. In a similar vein, an exemplary embodiment is such that the system of FIG. 19 is configured to execute any method detailed herein, or any one or more method actions of any method as applicable to the specific component of the system of FIG. 19.

Any device, system, and/or method of ascertaining the recipient's competence/comfort with respect to his or her utilization of the hearing prosthesis 100 can be utilized as a basis to change the content of the specific interface display/ present different displays. In at least some exemplary embodiments, statistically significant data is utilized as the basis to determine what should and should not be displayed on a given display/what display should be displayed.

Reference herein is frequently made to the recipient of a hearing prosthesis. It is noted that in at least some exemplary embodiments, the teachings detailed herein can be applicable to a person who is not the recipient of a hearing prosthesis. Accordingly, for purposes of shorthand, at least some exemplary embodiments include embodiments where the disclosures herein directed to a recipient correspond to a disclosure directed towards a person who is not a recipient but instead is only hard of hearing or otherwise has a hearing ailment.

In an exemplary embodiment, there is a method, comprising, evaluating speech of a recipient of a hearing prosthesis, the speech of the recipient corresponding to speech produced by the recipient during a first temporal period; and adjusting a hearing habilitation and/or rehabilitation regime of the recipient based on the evaluation. In an exemplary embodiment, there is a method as described above and/or below, wherein: the action of evaluating the speech of the recipient includes acoustically analyzing patterns in speech production of the recipient.

In an exemplary embodiment, there is a method as described above and/or below, wherein the action of evaluating the speech of the recipient includes comparing the speech of the recipient to speech of the recipient produced during a second temporal period prior to the first temporal period. In an exemplary embodiment, there is a method as described above and/or below, wherein the second temporal period is a period prior to an acquisition of the hearing prosthesis by the recipient. In an exemplary embodiment, there is a method as described above and/or below, further comprising evaluating non-speech related data, wherein the action of adjusting the hearing habilitation and/or rehabilitation regime of the recipient is also based on the evaluation of the non-speech related data. In an exemplary embodiment, there is a method as described above and/or below, wherein: the action of evaluating the speech of the recipient includes detecting at least one of speech articulation problems, phonological process problems or problems pronouncing sounds having relatively higher frequency components than that of other pronounced sounds. In an exemplary embodiment, there is a method as described above and/or below, wherein: the action of evaluating the speech of the recipient includes determining that the recipient is having problems hearing in a first set of sound conditions relative to that which is the case in a second set of sound conditions. In an exemplary embodiment, there is a method as described above and/or below, wherein: the action of evaluating speech of the recipient includes comparing the speech of the recipient to data of a speech development trajectory for similarly situated recipients.

In an exemplary embodiment, there is a body worn or implantable hearing prosthesis, comprising: a device configured to capture an audio environment of a recipient and evoke a hearing percept based at least in part on the captured audio environment, wherein the hearing prosthesis is configured to identify, based on the captured audio environment, one or more biomarkers present in the audio environment indicative of the recipient's ability to hear.

In an exemplary embodiment, there is a hearing prosthesis as described above and/or below, wherein the hearing prosthesis is configured to evaluate the one or more biomarkers and develop data indicative of the recipient's ability to speak. In an exemplary embodiment, there is a hearing prosthesis as described above and/or below, wherein: the audio environment includes speech of the recipient.

In an exemplary embodiment, there is a method, comprising: capturing first sounds corresponding to speech of a recipient of a hearing prosthesis; comparing the captured first sounds to data based on speech of others; and diagnosing a hearing-related impairment based on the comparison. In an exemplary embodiment, there is a method as described above and/or below, wherein: the hearing prosthesis is a cochlear implant; and the hearing related issue is a sub-performance map setting of the cochlear implant. In an exemplary embodiment, there is a method as described above and/or below, wherein: the hearing related issue is relative difficulty perceiving certain frequencies.

In an exemplary embodiment, there is a method, comprising: capturing sound with a hearing prosthesis; and evaluating the captured sound to determine the ability of the recipient of the hearing prosthesis to hear. In an exemplary embodiment, there is a method as described above and/or below, wherein: the action of evaluating the captured sound is executed invisibly to the recipient. In an exemplary embodiment, there is a method as described above and/or below, wherein: the action of evaluating the captured sound includes identifying biomarkers and comparing the biomarkers to a known reference to determine that the biomarker indicates that the recipient is having difficulty hearing.

Any disclosure herein of the hearing prosthesis executing one or more of the method actions detailed herein are having a disclosed functionality also corresponds to a disclosure of a remote device and/or a person executing those method actions. That is, by way of example only and not by way of limitation, the actions of the hearing prosthesis can be performed by another device, such as a smart phone, a personal computer, etc. Also, any disclosure of any remote device executing one or more the method actions detailed herein or otherwise having a disclosed functionality also corresponds to a disclosure of a hearing prosthesis having such functionality and/or being configured to execute such method actions, along with a disclosure of a person executing such method actions.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, and it is not otherwise noted that such is not the case.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
   capturing sound with a hearing prosthesis while the hearing prosthesis is used by a recipient; and
   evaluating the captured sound by at least identifying one or more linguistic characteristics of speech of the recipient and determining an ability of a recipient of the hearing prosthesis to hear based at least in part on an identified one or more linguistic characteristics of speech of the recipient identified as a result of the identifying one or more linguistic characteristics, wherein
   the recipient has a medical condition related to hearing, and the determination of the ability of the recipient of the hearing prosthesis to hear is part of a therapeutic hearing habilitation or rehabilitation treatment.

2. The method of claim 1, further providing:
   counseling the recipient based on the evaluation.

3. The method of claim 2, wherein:
   counseling includes at least one of:
      instructing the recipient under what scenarios he or she should pay more attention to people's lips during conversations relative to other times; or
      instructing the recipient under what scenarios to increase a volume of the hearing prosthesis of the recipient relative to other times.

4. The method of claim 2, wherein:
   counseling includes counseling the recipient to pay closer attention to people's lips when the recipient is located in a building.

5. The method of claim 1, further comprising:
   adjusting the hearing habilitation and/or rehabilitation treatment based on the evaluation.

6. The method of claim 1, wherein:
   evaluating the captured sound is executed by the hearing prosthesis; and
   the method further includes automatically adjusting a feature of the hearing prosthesis based on the evaluation.

7. The method of claim 1, wherein:
   evaluating is executed by an audiologist.

8. The method of claim 1, wherein:
   evaluating the captured sound consists of evaluating captured sound that is speech of others other than the recipient.

9. A method, comprising:
capturing sound with a hearing prosthesis while the hearing prosthesis is used by a recipient; and
evaluating the captured sound to determine an ability of the recipient of the hearing prosthesis to hear based at least in part on analysis of at least one of phoneme errors, frequency, intonation or substation errors, wherein
the recipient has a medical condition related to hearing, and the determination of the ability of the recipient of the hearing prosthesis to hear is part of a therapeutic hearing habilitation or rehabilitation treatment.

10. The method of claim 9, wherein:
the evaluating of the captured sound to determine an ability of the recipient of the hearing prosthesis to hear is based at least in part on analysis of at least two of phoneme errors, frequency, intonation or substation errors.

11. The method of claim 9, wherein:
the evaluating of the captured sound to determine an ability of the recipient of the hearing prosthesis to hear is based at least in part on analysis of at least three of phoneme errors, frequency, intonation or substation errors.

12. A method, comprising:
capturing sound with a hearing prosthesis while the hearing prosthesis is used by a recipient of the hearing prosthesis; and
evaluating the captured sound to determine an ability of the recipient of the hearing prosthesis to hear, wherein
the recipient has a medical condition related to hearing, and the determination of the ability of the recipient of the hearing prosthesis to hear is part of a therapeutic hearing habilitation or rehabilitation treatment.

13. The method of claim 12, wherein:
evaluating the captured sound includes comparing the captured sound that is speech of others other than the recipient to speech to speech of the recipient.

14. The method of claim 13, further comprising:
determining, based on results of the evaluation, that the recipient should increase exposure time to more-complex sounds relative to that which has been previously the case.

15. The method of claim 12, wherein:
the determination of the ability of the recipient to hear is based on analysis of phoneme errors, and the therapeutic hearing habilitation or rehabilitation treatment includes high level speech exercises.

16. The method of claim 15, further comprising:
implementing a clinical management action of adjusting a comfort level of the hearing prosthesis of the recipient based on the identification of the phoneme error.

17. The method of claim 12, wherein:
evaluating the captured sound to determine the ability of the recipient to hear includes comparing the captured sound to a statistically significant model.

18. The method of claim 12, wherein:
evaluating the captured sound is real-time evaluation relative to the capturing of sound.

19. The method of claim 12, wherein:
the determination of the ability of the recipient to hear is based on analysis of phoneme errors, and the therapeutic hearing habilitation or rehabilitation treatment includes soft level speech exercises.

20. The method of claim 12, wherein:
the determination of the ability of the recipient to hear is based on analysis of frequency;
the determination of the ability of the recipient to hear is also based on analysis of intonation;
the determination of the ability of the recipient to hear is also based on analysis of substitution errors; and
the therapeutic hearing habilitation or rehabilitation treatment includes intonation exercises.

21. A method, comprising:
capturing sound with a hearing prosthesis; and
evaluating the captured sound to determine an ability of a recipient of the hearing prosthesis to hear based at least in part on analysis of one or more of phoneme errors, frequency, intonation or substation errors, wherein
the recipient has a medical condition related to hearing, and the determination of the ability of the recipient of the hearing prosthesis to hear is part of a therapeutic hearing habilitation or rehabilitation treatment.

22. The method of claim 21, further comprising:
diagnosing a hearing-related impairment based on the evaluation.

23. The method of claim 21, wherein:
the ability of the recipient to hear is an ability of the recipient to hear certain frequencies.

24. The method of claim 19, further comprising:
implementing a clinical management action of disabling an electrode of the hearing prosthesis of the recipient based on the identification of frequency, and based on the identification of intonation and based on the identification of substitution errors.

25. The method of claim 21, wherein:
the recipient has experienced a relatively sudden hearing loss in higher sound frequencies; and
evaluating the captured sound includes evaluating speech of the recipient and determining, based on the evaluation of the speech, that the recipient has undergone the relatively sudden hearing loss in the higher sound frequencies.

* * * * *